United States Patent
Lee et al.

(10) Patent No.: US 8,357,482 B2
(45) Date of Patent: Jan. 22, 2013

(54) ORGANIC ANTI-REFLECTIVE LAYER COMPOSITION CONTAINING RING-OPENED PHTHALIC ANHYDRIDE AND METHOD FOR PREPARATION THEREOF

(75) Inventors: Jong-Don Lee, Asan-si (KR); Jun-Ho Lee, Asan-si (KR); Shin-Hyo Bae, Asan-si (KR); Seung-Hee Hong, Asan-si (KR); Seung-Duk Cho, Asan-si (KR)

(73) Assignee: Korea Kumho Petrochemical Co., Ltd., Seoul (KR)

( * ) Notice: Subject to any disclaimer, the term of this patent is extended or adjusted under 35 U.S.C. 154(b) by 0 days.

(21) Appl. No.: 13/186,101

(22) Filed: Jul. 19, 2011

(65) Prior Publication Data

US 2011/0272643 A1 Nov. 10, 2011

Related U.S. Application Data

(62) Division of application No. 12/321,091, filed on Jan. 15, 2009.

(30) Foreign Application Priority Data

Aug. 26, 2008 (KR) .................. 10-2008-0083295

(51) Int. Cl.
| | |
|---|---|
| G02B 5/22 | (2006.01) |
| C08K 5/03 | (2006.01) |
| C08L 33/00 | (2006.01) |
| C08L 63/00 | (2006.01) |

(52) U.S. Cl. ............ 430/271.1; 252/582; 430/311; 430/330; 430/326; 525/438

(58) Field of Classification Search ............ None
See application file for complete search history.

(56) References Cited

U.S. PATENT DOCUMENTS

2004/0101779 A1* 5/2004 Wu et al. ............ 430/271.1
2006/0058468 A1* 3/2006 Wu et al. ............ 525/386
2009/0186294 A1* 7/2009 Goldfarb et al. ....... 430/270.1

* cited by examiner

Primary Examiner — Cynthia Hamilton
(74) Attorney, Agent, or Firm — Davidson, Davidson & Kappel, LLC

(57) ABSTRACT

A light absorbent for forming an organic anti-reflective layer, represented by the following formula 1 or formula 2, is provided:

[Formula 1]

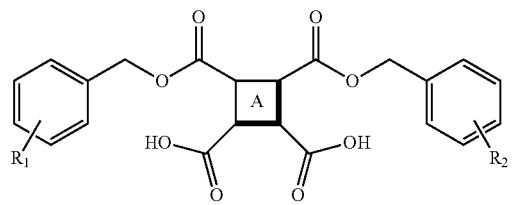

[Formula 2]

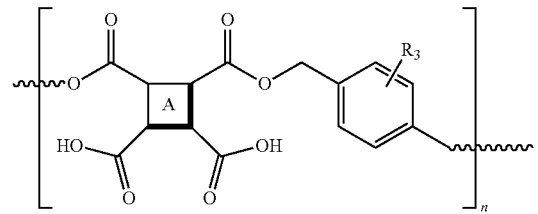

wherein A represents a substituted or unsubstituted, linear or branched, saturated tetravalent hydrocarbon group, a substituted or unsubstituted, linear or branched, saturated hydrocarbon group and containing one or more heteroatoms, a substituted or unsubstituted aromatic group, a substituted or unsubstituted heteroaromatic group, a substituted or unsubstituted alicyclic group, a substituted or unsubstituted heteroalicyclic group, a substituted or unsubstituted diaryl ether, a substituted or unsubstituted diaryl sulfide, a substituted or unsubstituted diaryl sulfoxide, a substituted or unsubstituted diaryl ketone, or a substituted or unsubstituted diaryl bisphenol A; $R_1$, $R_2$, and $R_3$ each independently represent a hydrogen atom, a halogen atom, a substituted or unsubstituted alkyl group, a substituted or unsubstituted aryl group, a substituted or unsubstituted acetal group, or a substituted or unsubstituted hydroxyl group; and n is an integer from 2 to 500.

5 Claims, 9 Drawing Sheets

ORGANIC ANTI-REFLECTIVE LAYER COMPOSITION CONTAINING RING-OPENED PHTHALIC ANHYDRIDE AND METHOD FOR PREPARATION THEREOF

This application is a divisional of U.S. patent application Ser. No. 12/321,091 which claims priority under 35 U.S.C §119 from Korean Patent Application 10-2008-0083295, filed on Aug. 26, 2008, the contents of which are hereby incorporated by reference in their entirety for all purposes as if fully set forth herein.

BACKGROUND OF THE INVENTION

1. Field of the Invention

The present invention relates to a novel light absorbent for forming an organic anti-reflective layer, which is a ring-opened phthalic anhydride compound, an organic anti-reflective layer composition, a method for patterning a semiconductor device using the organic anti-reflective layer composition, and a semiconductor device produced by the method for patterning. More particularly, the present invention relates to a novel light absorbent capable of being used in producing an organic anti-reflective layer which is useful for the formation of ultrafine semiconductor patterns using an ArF excimer laser; an organic anti-reflective layer composition containing the light absorbent, which prevents reflection from underneath film layers in lithographic processes, prevents a stationary wave, and exhibits a high dry etching rate; a method for patterning a semiconductor device using the organic anti-reflective layer composition; and a semiconductor device produced by the method for patterning.

2. Description of the Related Art

Along with the recent high integration of semiconductor devices, there is a demand for ultrafine patterns with a line width of 0.10 micrometers or less in the production of ultra LSI and the like, and a demand also exists for lithographic processes using light of lower wavelengths in the region of conventionally used g-ray or i-ray as the exposure wavelength. Accordingly, microlithographic processes using KrF excimer lasers and ArF excimer lasers are currently used for the process for producing semiconductor devices.

Because the size of patterns of semiconductor devices is ever decreasing, only when the reflectance is maintained to be at least less than 1% while the exposure process is carried out, a uniform pattern can be obtained, and an appropriate process window can be obtained, so as to attain a desired yield.

Therefore, technologies of preventing reflection from underneath film layers and eliminating a stationary wave, by disposing an organic anti-reflective layer containing organic molecules which are capable of absorbing light, beneath a photoresist layer, to thereby control the reflectance so as to reduce the reflectance at the maximum, have become important.

SUMMARY OF THE INVENTION

In order to overcome such problems as described above, it is an object of the present invention to provide a novel light absorbent which can be used in an organic anti-reflective layer capable of absorbing reflected light that is generated during exposure in ultrafine patterning lithographic processes making use of 193-nm ArF excimer laser, and an organic anti-reflective layer composition comprising the light absorbent.

It is another object of the invention to provide a method of designing the basic structure of an organic anti-reflective layer to constitute a chemical structure capable of increasing the etching rate of the organic anti-reflective layer, and producing a polymer in accordance therewith, to thus produce an organic anti-reflective layer using the polymer, so that etching processes can be carried out more smoothly, and to provide a method for forming a pattern of a semiconductor device using the organic anti-reflective layer composition, which method is capable of achieving the formation of excellent ultrafine patterns by eliminating undercut, footing and the like.

According to an aspect of the present invention, there is provided a light absorbent for forming an organic anti-reflective layer, represented by the following formula 1:

[Formula 1]

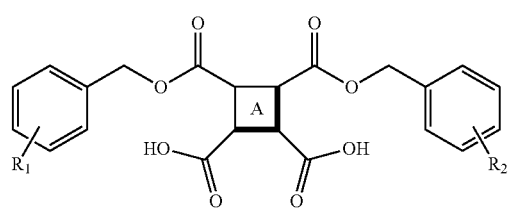

wherein A represents a substituted or unsubstituted, linear or branched, saturated tetravalent hydrocarbon group having 1 to 20 carbon atoms, a substituted or unsubstituted, linear or branched, saturated hydrocarbon group having 1 to 20 carbon atoms and containing one or more heteroatoms, a substituted or unsubstituted aromatic group having 4 to 20 carbon atoms, a substituted or unsubstituted heteroaromatic group having 3 to 20 carbon atoms, a substituted or unsubstituted alicyclic group having 4 to 20 carbon atoms, a substituted or unsubstituted heteroalicyclic group having 3 to 20 carbon atoms, a substituted or unsubstituted diaryl ether having 3 to 20 carbon atoms, a substituted or unsubstituted diaryl sulfide having 3 to 20 carbon atoms, a substituted or unsubstituted diaryl sulfoxide having 3 to 20 carbon atoms, a substituted or unsubstituted diaryl ketone having 3 to 20 carbon atoms, or a substituted or unsubstituted diaryl bisphenol A having 3 to 20 carbon atoms; and $R_1$ and $R_2$ each independently represent a hydrogen atom, a halogen atom, a substituted or unsubstituted alkyl group having 1 to 10 carbon atoms, a substituted or unsubstituted aryl group having 6 to 14 carbon atoms, a substituted or unsubstituted acetal group, or a substituted or unsubstituted hydroxyl group.

According to another aspect of the present invention, there is provided a light absorbent for forming an organic anti-reflective layer, represented by the following formula 2:

[Formula 2]

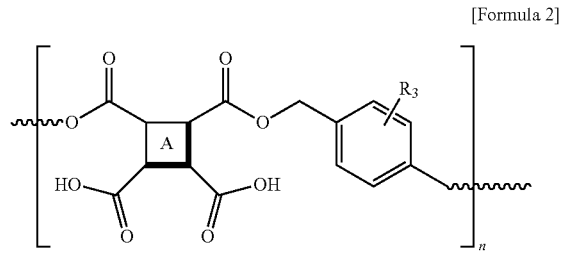

wherein A represents a substituted or unsubstituted, linear or branched, saturated tetravalent hydrocarbon group having 1 to 20 carbon atoms, a substituted or unsubstituted, linear or branched, saturated hydrocarbon group having 1 to 20 carbon atoms and containing one or more heteroatoms, a substituted or unsubstituted aromatic group having 4 to 20 carbon atoms, a substituted or unsubstituted heteroaromatic group having 3 to 20 carbon atoms, a substituted or unsubstituted alicyclic group having 4 to 20 carbon atoms, a substituted or unsubstituted heteroalicyclic group having 3 to 20 carbon atoms, a substituted or unsubstituted diaryl ether having 3 to 20 carbon atoms, a substituted or unsubstituted diaryl sulfide having 3 to 20 carbon atoms, a substituted or unsubstituted diaryl sulfoxide having 3 to 20 carbon atoms, a substituted or unsubstituted diaryl ketone having 3 to 20 carbon atoms, or a substituted or unsubstituted diaryl bisphenol A having 3 to 20 carbon atoms; $R_3$ represents a hydrogen atom, a halogen atom, a substituted or unsubstituted alkyl group having 1 to 10 carbon atoms, a substituted or unsubstituted aryl group having 6 to 14 carbon atoms, a substituted or unsubstituted acetal group, or a substituted or unsubstituted hydroxyl group; and n is an integer from 2 to 500.

According to another aspect of the present invention, there is provided an organic anti-reflective composition comprising the light absorbent represented by the formula 1 or formula 2, a polymer, a thermal acid generating agent, a crosslinking agent, and a solvent.

According to another aspect of the present invention, there is provided a method for patterning a semiconductor device, the method comprising:

applying the organic anti-reflective layer composition according to the present invention on top of a layer to be etched;

curing the applied composition through a baking process, and forming crosslinking bonds to form an organic anti-reflective layer;

applying a photoresist on top of the organic anti-reflective layer, and exposing and developing the photoresist to form a photoresist pattern; and etching the organic anti-reflective layer using the photoresist pattern as an etching mask, and then etching the layer to be etched so as to pattern the layer to be etched.

According to another aspect of the present invention, there is provided a semiconductor device produced by the method for patterning according to the present invention.

The organic anti-reflective layer composition according to the present invention exhibits excellent adhesiveness and storage stability, as well as excellent resolution in both C/H patterns and L/S patterns. The organic anti-reflective layer composition also has an excellent process window, so that excellent pattern profiles can be obtained irrespective of the type of the substrate.

Furthermore, when a pattern is formed using the organic anti-reflective layer composition, etching of the anti-reflective layer can be rapidly carried out in ultrafine patterning processes making use of a 193-nm light source, and as a result, development of high integration semiconductor devices can be achieved more actively.

DESCRIPTION OF THE PREFERRED EMBODIMENTS

Figure 1:
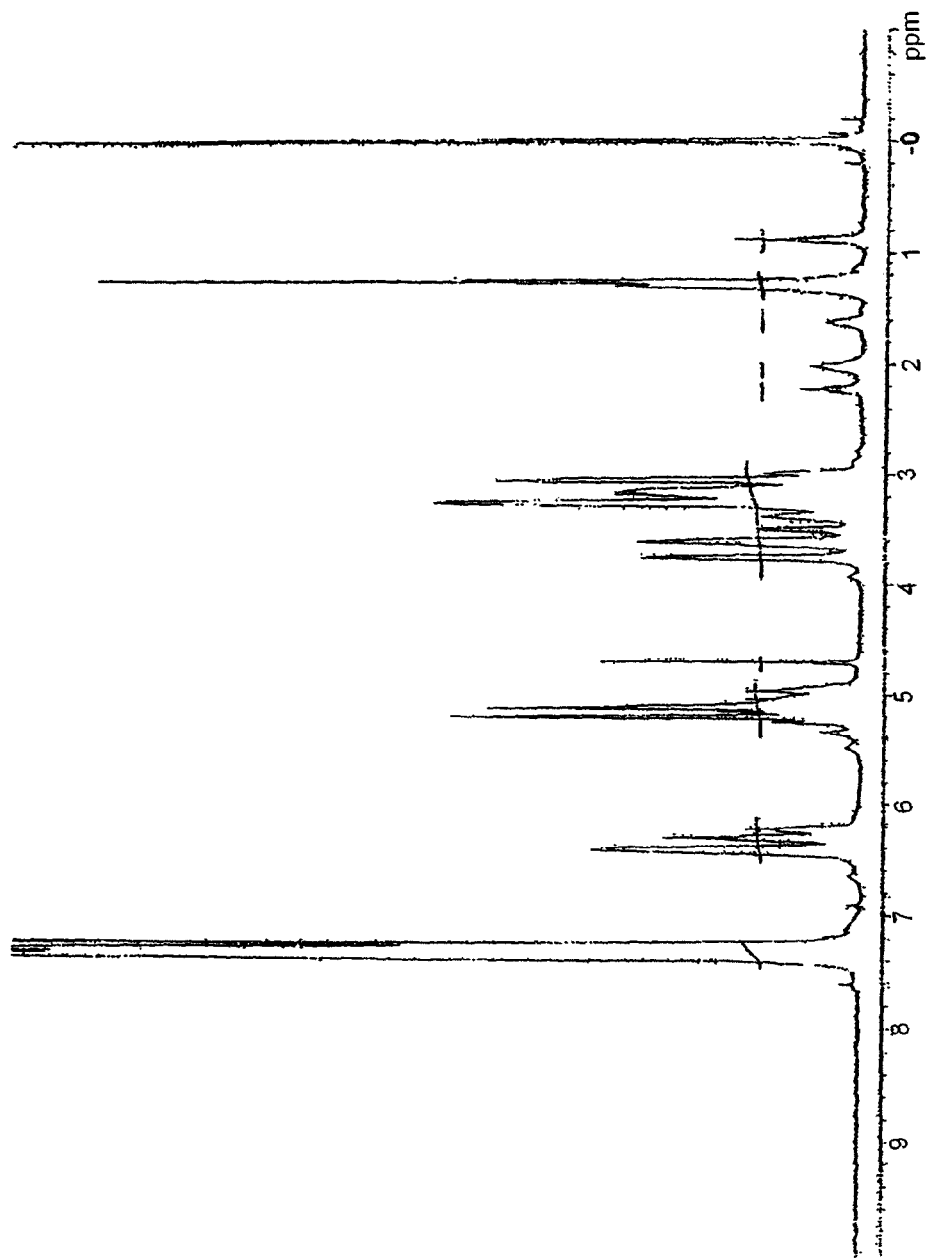
FIG. 1 is a $^1$H-NMR spectrum of a copolymer produced according to an embodiment of the present invention.

Hereinafter, the present invention will be described in more detail.

According to an aspect of the present invention, a ring-opened phthalic anhydride represented by the following formula 1, which serves as a light absorbent for forming an organic anti-reflective layer, is provided.

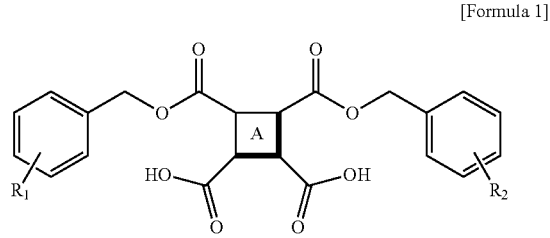

[Formula 1]

wherein A represents a substituted or unsubstituted, linear or branched, saturated tetravalent hydrocarbon group having 1 to 20 carbon atoms, a substituted or unsubstituted, linear or branched, saturated hydrocarbon group having 1 to 20 carbon atoms and containing one or more heteroatoms, a substituted or unsubstituted aromatic group having 4 to 20 carbon atoms, a substituted or unsubstituted heteroaromatic group having 3 to 20 carbon atoms, a substituted or unsubstituted alicyclic group having 4 to 20 carbon atoms, a substituted or unsubstituted heteroalicyclic group having 3 to 20 carbon atoms, a substituted or unsubstituted diaryl ether having 3 to 20 carbon atoms, a substituted or unsubstituted diaryl sulfide having 3 to 20 carbon atoms, a substituted or unsubstituted diaryl sulfoxide having 3 to 20 carbon atoms, a substituted or unsubstituted diaryl ketone having 3 to 20 carbon atoms, or a substituted or unsubstituted diaryl bisphenol A having 3 to 20 carbon atoms; and $R_1$ and $R_2$ each independently represent a hydrogen atom, a halogen atom, a substituted or unsubstituted alkyl group having 1 to 10 carbon atoms, a substituted or unsubstituted aryl group having 6 to 14 carbon atoms, a substituted or unsubstituted acetal group, or a substituted or unsubstituted hydroxyl group.

According to another aspect of the present invention, a ring-opened phthalic anhydride compound represented by the following formula 2, which serves as a light absorbent for forming an organic anti-reflective layer, is provided.

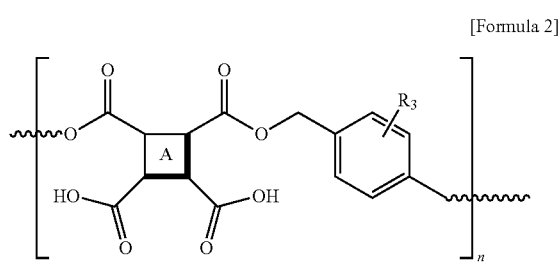

[Formula 2]

wherein A represents a substituted or unsubstituted, linear or branched, saturated tetravalent hydrocarbon group having 1 to 20 carbon atoms, a substituted or unsubstituted, linear or branched, saturated hydrocarbon group having 1 to 20 carbon atoms and containing one or more heteroatoms, a substituted or unsubstituted aromatic group having 4 to 20 carbon atoms, a substituted or unsubstituted heteroaromatic group having 3 to 20 carbon atoms, a substituted or unsubstituted alicyclic group having 4 to 20 carbon atoms, a substituted or unsubstituted heteroalicyclic group having 3 to 20 carbon atoms, a substituted or unsubstituted diaryl ether having 3 to 20 carbon atoms, a substituted or unsubstituted diaryl sulfide having 3 to 20 carbon atoms, a substituted or unsubstituted diaryl sulfoxide having 3 to 20 carbon atoms, a substituted or unsubstituted diaryl ketone having 3 to 20 carbon atoms, or a substituted or unsubstituted diaryl bisphenol A having 3 to 20 carbon atoms; $R_3$ represents a hydrogen atom, a halogen atom, a substituted or unsubstituted alkyl group having 1 to 10 carbon atoms, a substituted or unsubstituted aryl group having 6 to 14 carbon atoms, a substituted or unsubstituted acetal group, or a substituted or unsubstituted hydroxyl group; and n is an integer from 2 to 500, and preferably an integer from 2 to 300.

Preferably, the compound of formula 2 has a weight average molecular weight of 350 to 100,000, and more preferably 400 to 50,000.

The light absorbent contained in an organic anti-reflective layer can be classified into a type in which the light absorbent is included in a compound in the form of a chemical moiety capable of absorbing light, and a type in which the light absorbent is separately present with a polymer incapable of absorbing light. Typically, the light absorbent is separately used so that the amount of the light absorbing chemical species can be controlled.

The light absorbent of the present invention includes a benzene chromophore, and contains functional groups for thermal curing.

Specifically, since benzene chromophore derivatives may have widely varying etching properties depending on the structure, derivatives having various structures have been introduced in the present invention for the application in the organic anti-reflective layer composition.

Upon examining the reaction between the above-described light absorbent according to the present invention and a thermally curable compound which is a polymer to be contained in the anti-reflective layer composition as will be described later, a carboxylic acid functional group is generated by ring-opening of the light absorbent by means of an alcohol compound, and this carboxylic acid functional group reacts with a functional group of the thermally curable compound, such as acetal, epoxy or hemiacetal, to form a crosslinked structure.

The term "substituted" according to the present invention means that one or more hydrogen atoms in a group may be respectively substituted with a halogen atom, a hydroxyl group, a nitro group, a cyano group, an amino group, an amidino group, hydrazine, hydrazone, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkenyl group, a $C_1$-$C_{10}$ alkynyl group, a $C_6$-$C_{20}$ aryl group, a $C_7$-$C_{20}$ arylalkyl group, a $C_4$-$C_{20}$ heteroaryl group or a $C_5$-$C_{20}$ heteroarylalkyl group.

Specific examples of the light absorbent for forming an organic anti-reflective layer, represented by the formula 1, according to the present invention include compounds of the following formulas 3 to 42.

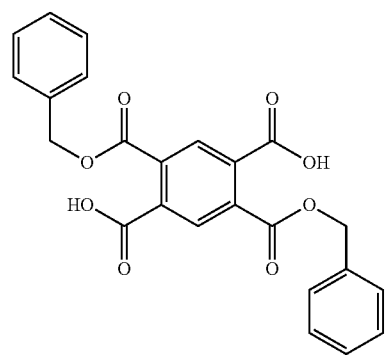

[Formula 3]

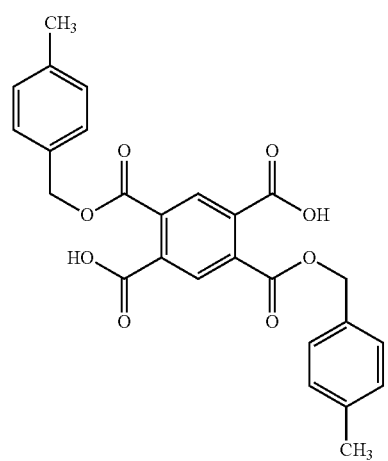

[Formula 4]

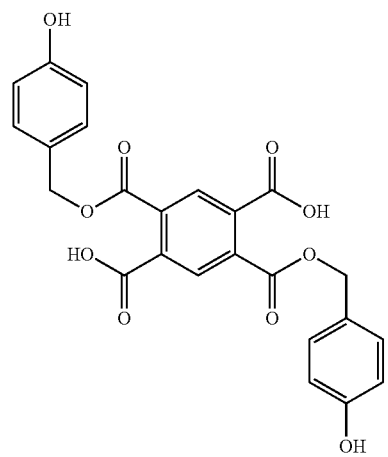

[Formula 5]

[Formula 6]
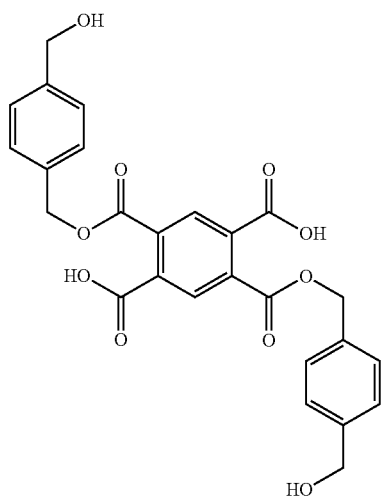
[Formula 9]
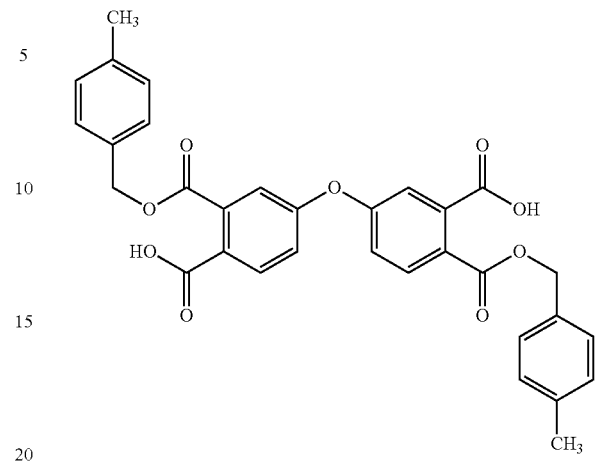
[Formula 7]
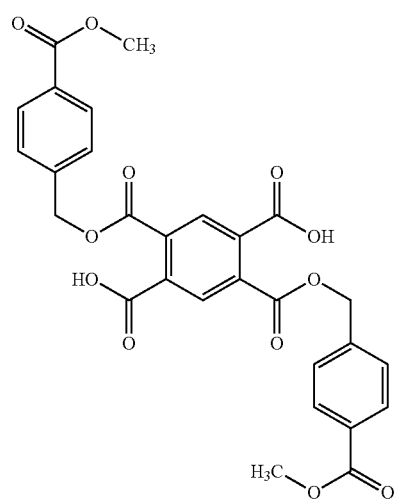
[Formula 10]
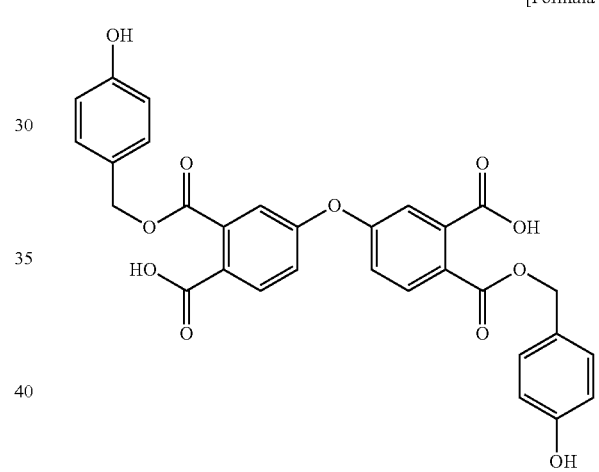
[Formula 8]
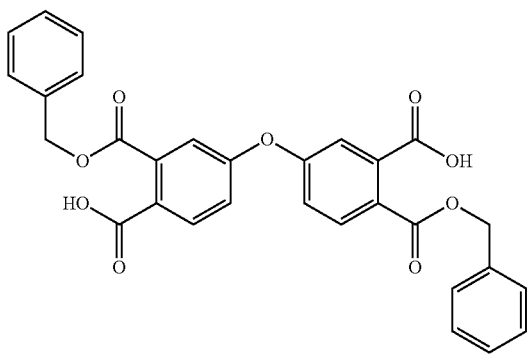
[Formula 11]
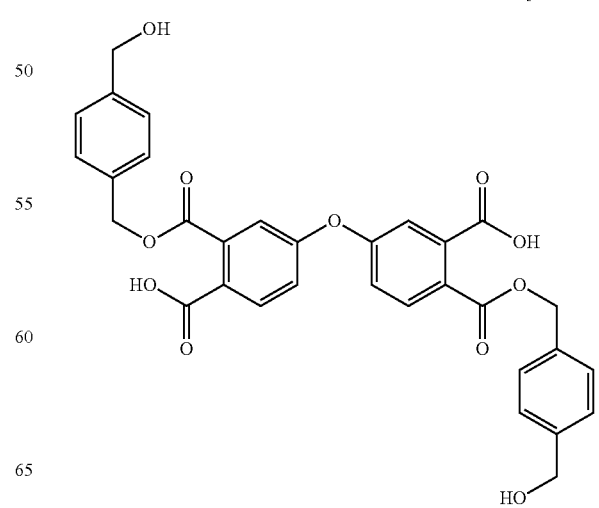

[Formula 12]
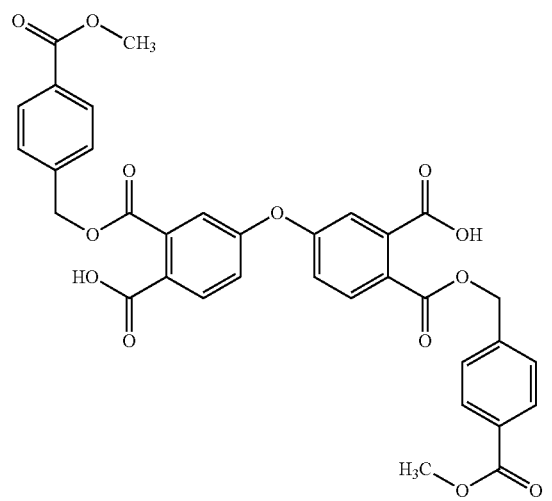
[Formula 13]
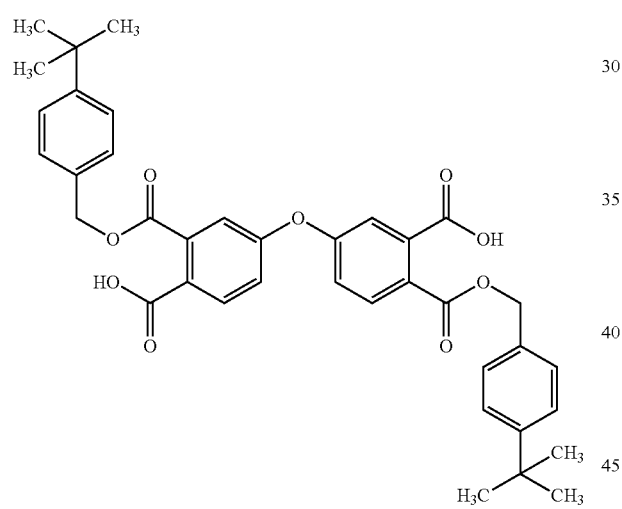
[Formula 14]
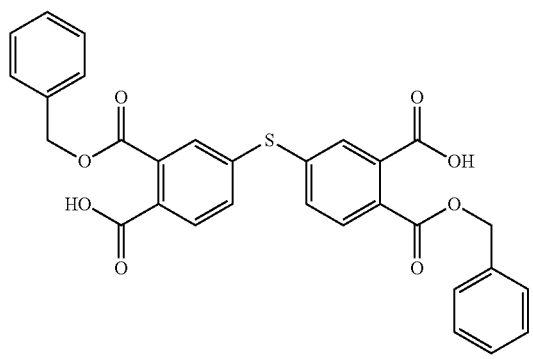
[Formula 15]
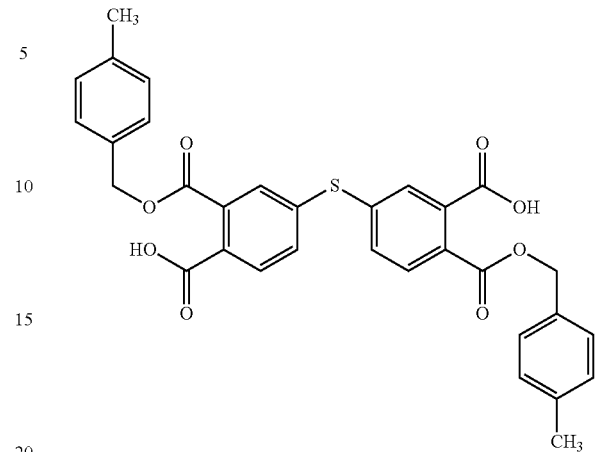
[Formula 16]
[Formula 17]
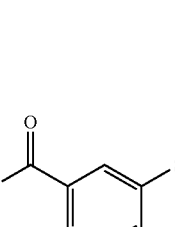

[Formula 18]
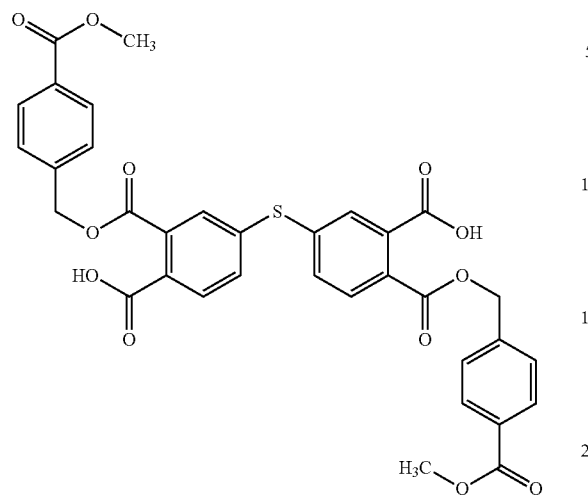
[Formula 19]
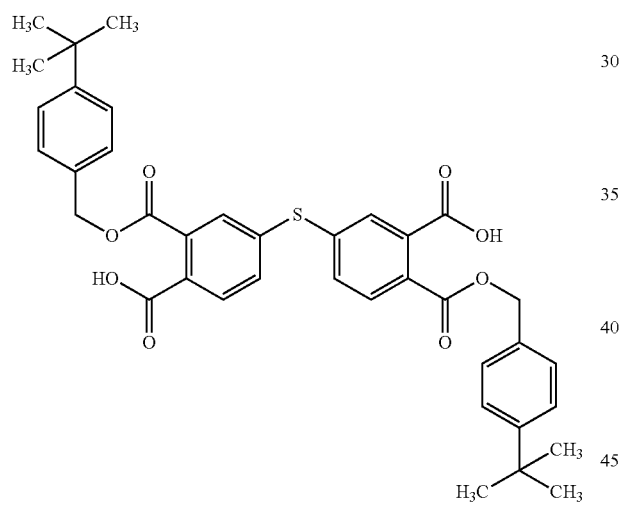
[Formula 20]
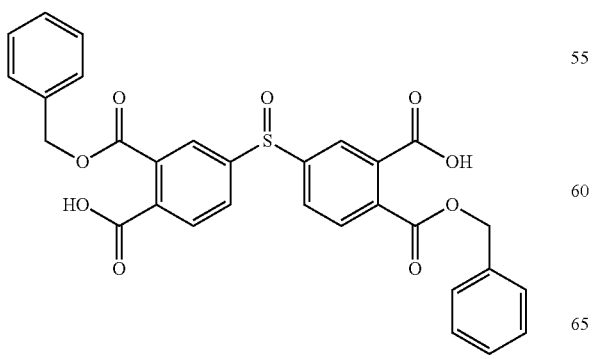
[Formula 21]
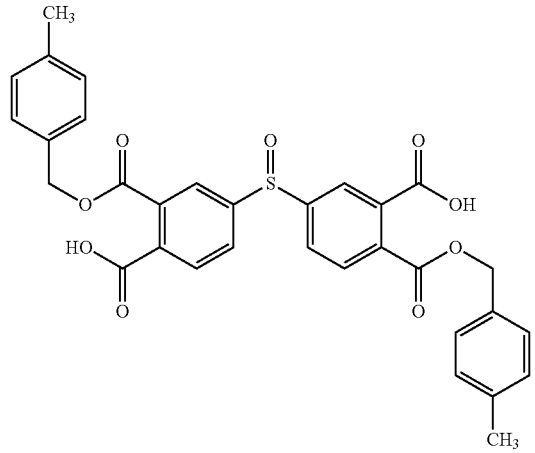
[Formula 22]
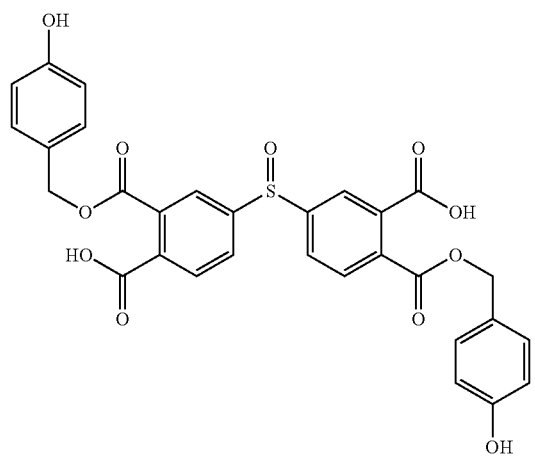
[Formula 23]
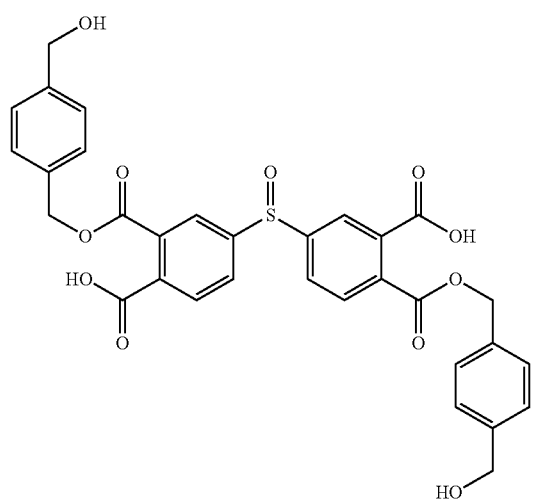

[Formula 24]
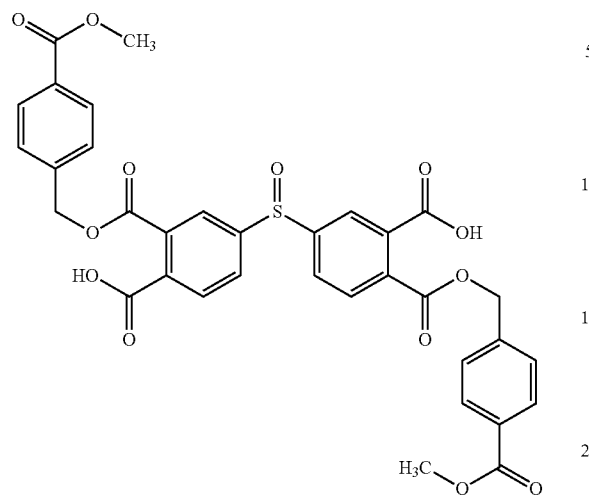
[Formula 25]
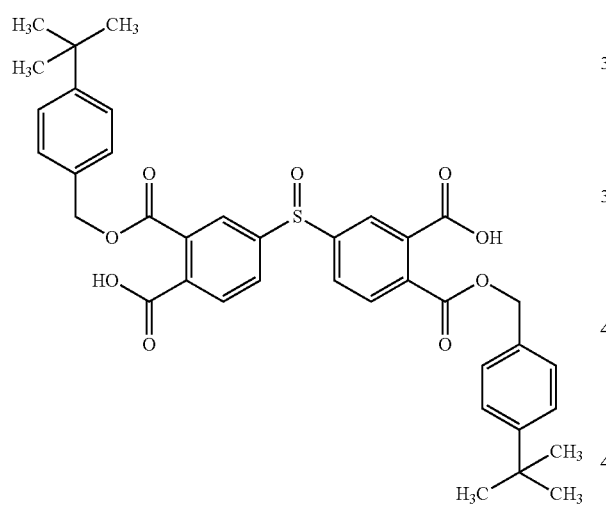
[Formula 26]
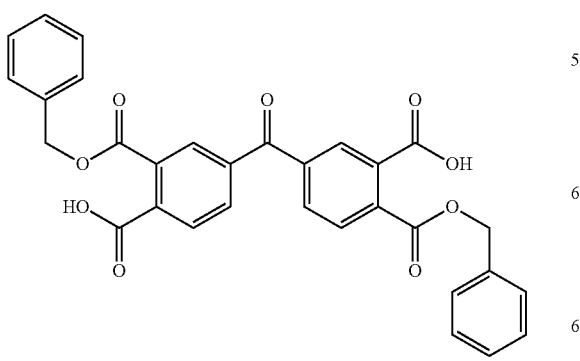
[Formula 27]
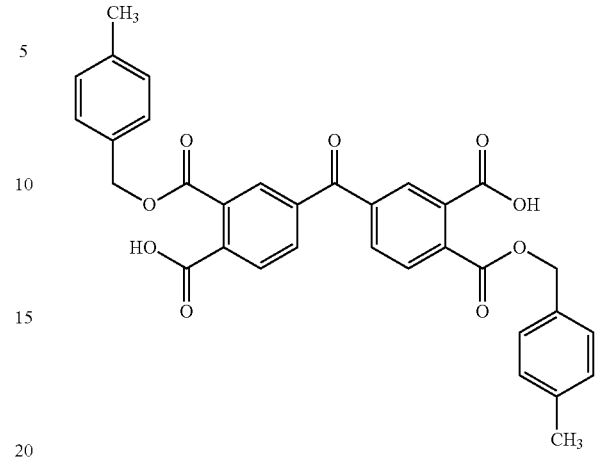
[Formula 28]
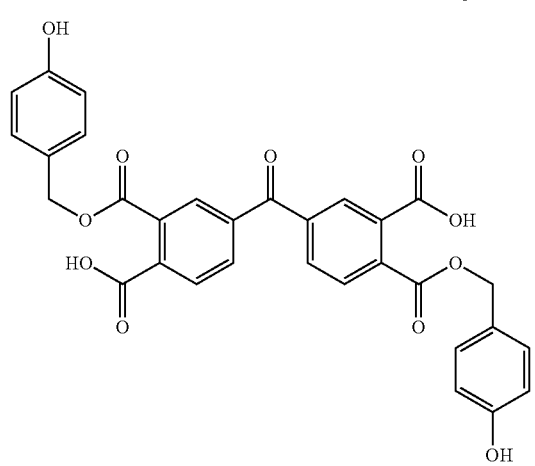
[Formula 29]
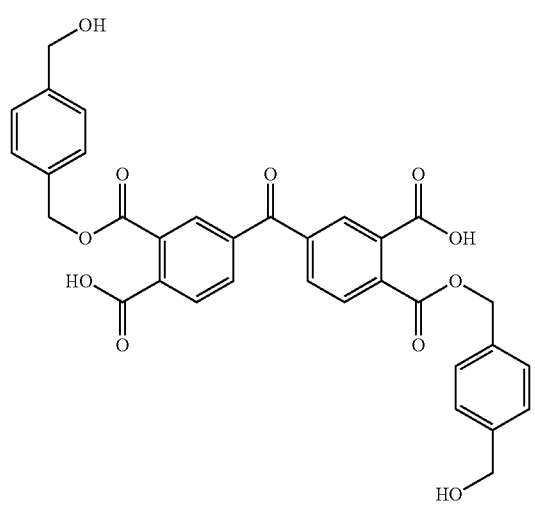

[Formula 30]
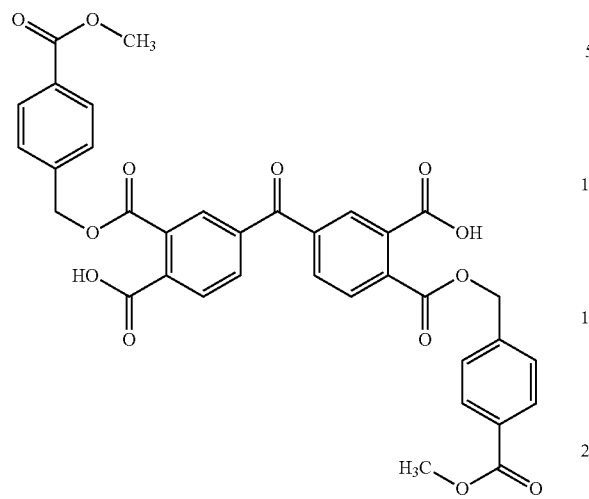
[Formula 31]
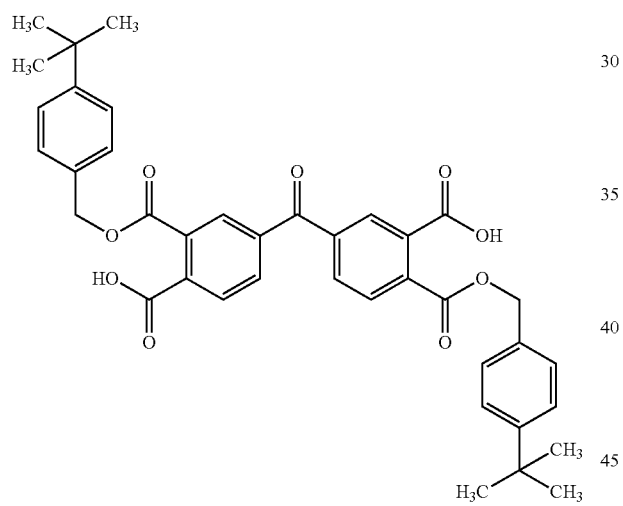
[Formula 32]
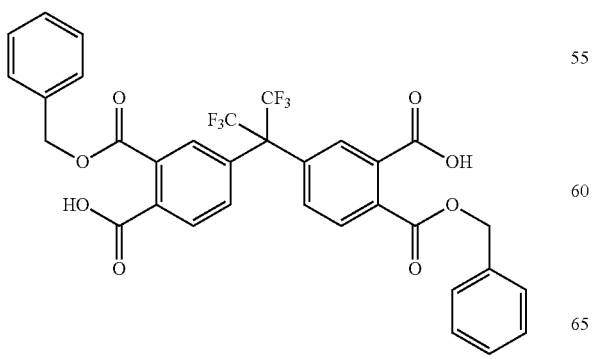
[Formula 33]
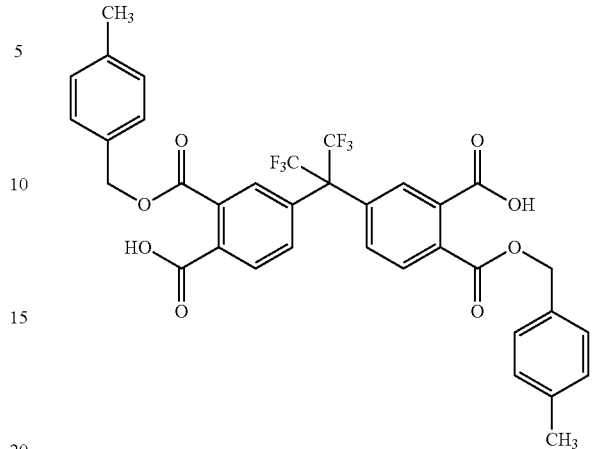
[Formula 34]
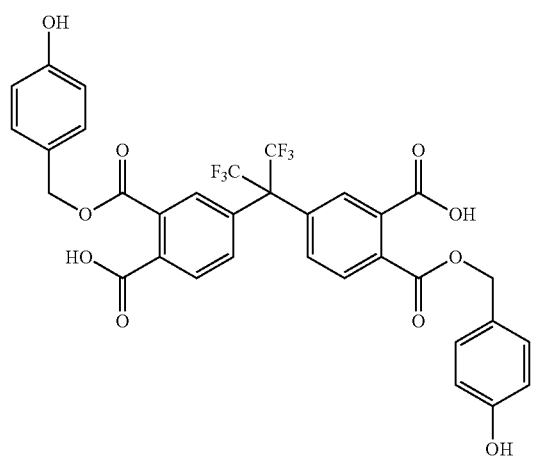
[Formula 35]
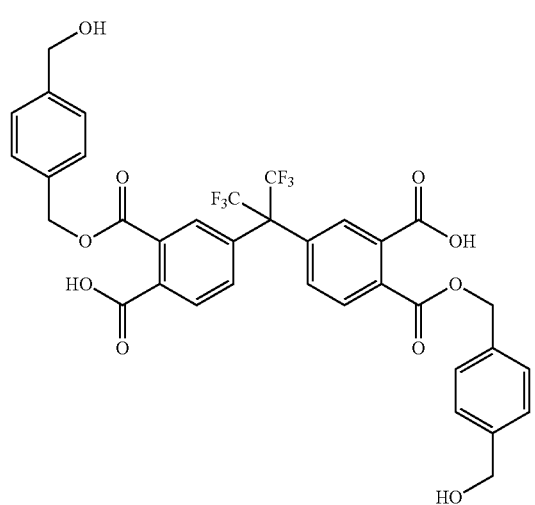

[Formula 36]
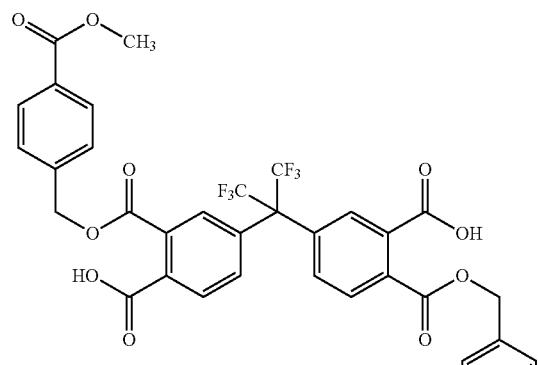
[Formula 37]
[Formula 38]
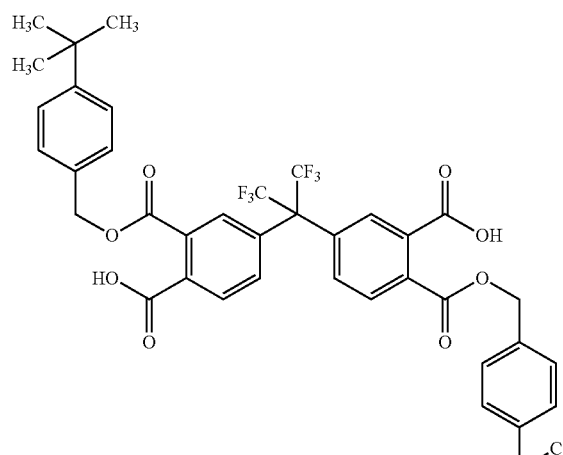
[Formula 39]
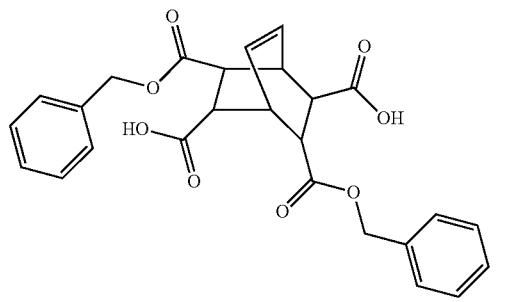
[Formula 40]
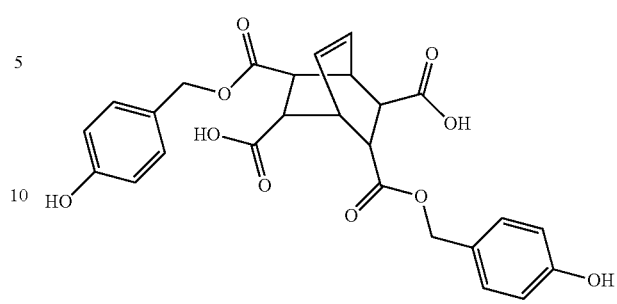
[Formula 41]
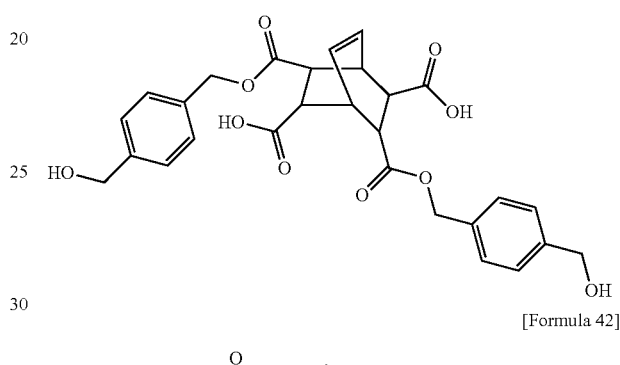
[Formula 42]
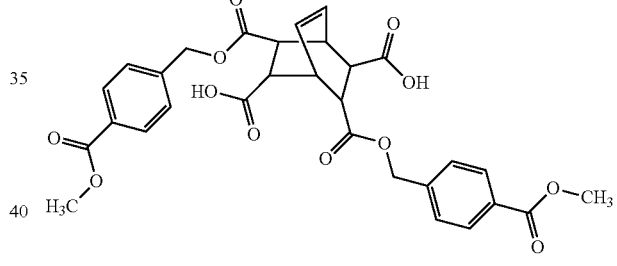
Furthermore, specific examples of the light absorbent for forming an organic anti-reflective layer, represented by the formula 2, according to the present invention include compounds of the following formulas 43 to 60.
[Formula 43]
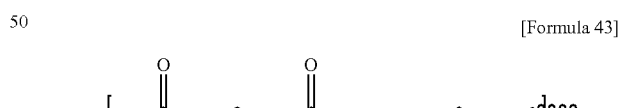
[Formula 44]
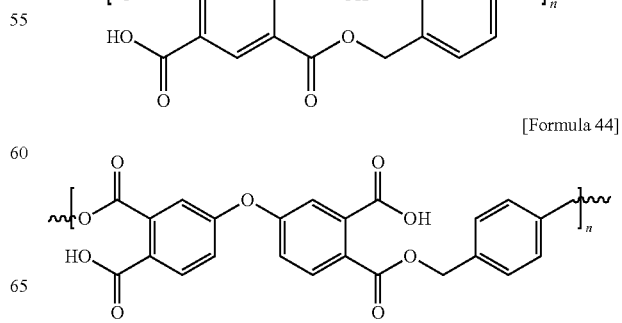

[Formula 45]
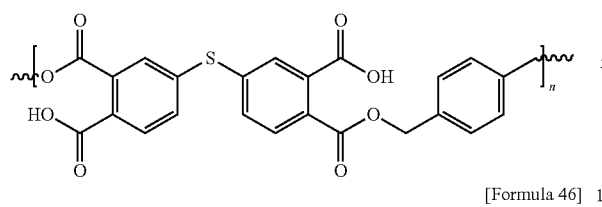
[Formula 46]
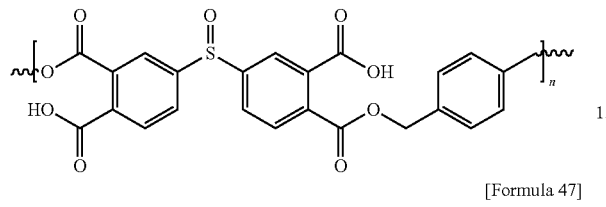
[Formula 47]
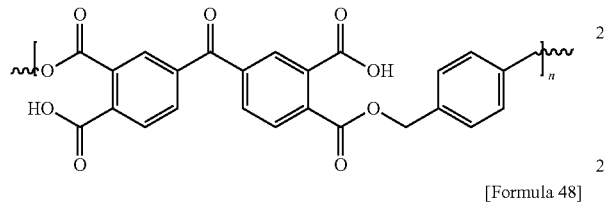
[Formula 48]
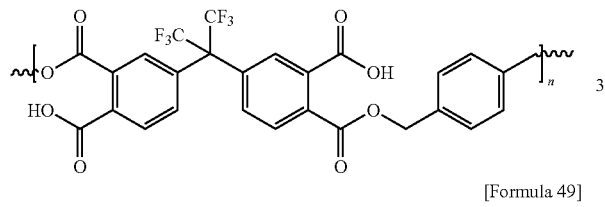
[Formula 49]
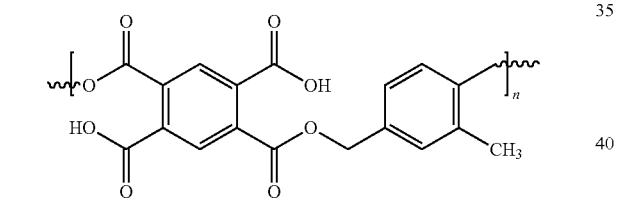
[Formula 50]
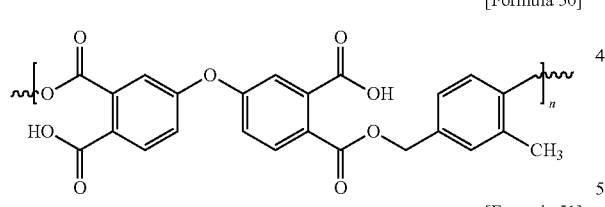
[Formula 51]
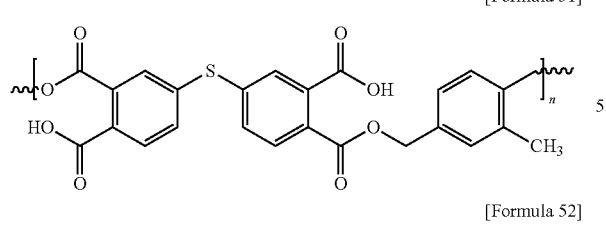
[Formula 52]
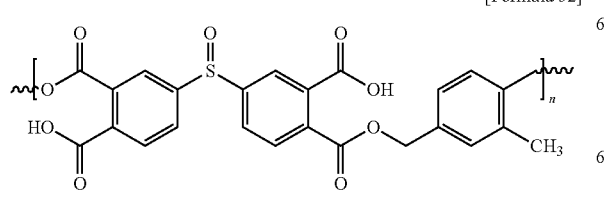
[Formula 53]
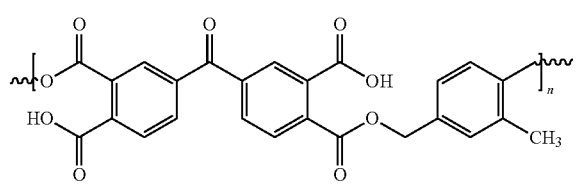
[Formula 54]
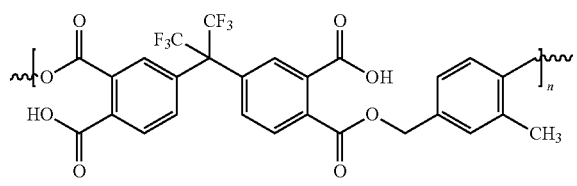
[Formula 55]
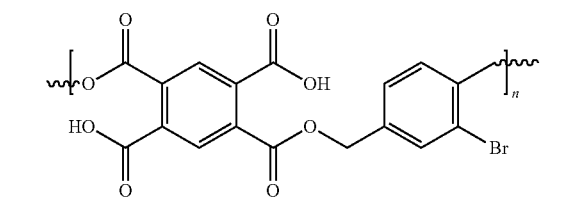
[Formula 56]
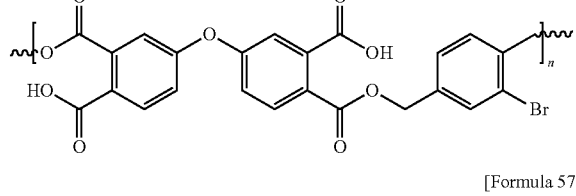
[Formula 57]
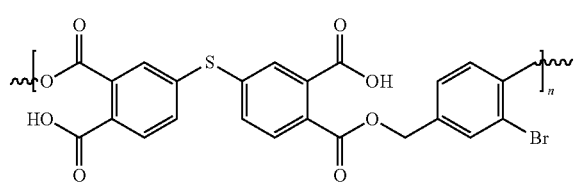
[Formula 58]
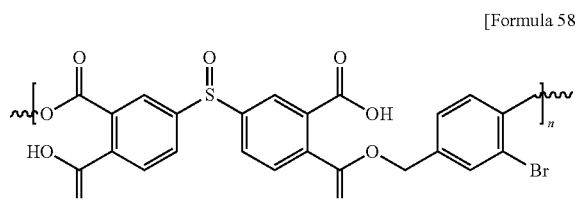
[Formula 59]
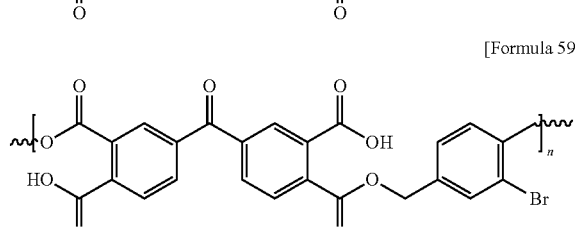

[Formula 60]

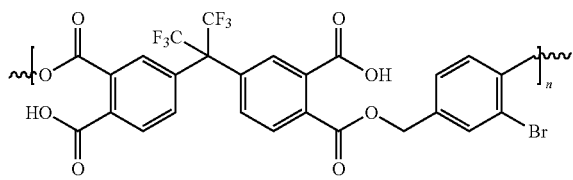

According to an embodiment of the present invention, the compounds represented by formula 1 of the present invention are produced by reacting a substituted or unsubstituted benzyl alcohol compound represented by the following formula 61 with various dianhydride compounds in the presence of a base, and then neutralizing the base used with an acid.

[Formula 61]

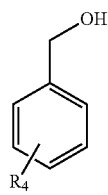

wherein $R_4$ represents a hydrogen atom, a halogen atom, a substituted or unsubstituted alkyl group having 1 to 10 carbon atoms, a substituted or unsubstituted aryl group having 6 to 14 carbon atoms, a substituted or unsubstituted acetal group, or a substituted or unsubstituted hydroxyl group.

According to another embodiment of the present invention, the compounds represented by formula 2 of the present invention can be produced by reacting a compound represented by the following formula 62 with various dianhydride compounds.

[Formula 62]

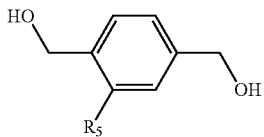

wherein $R_5$ represents a hydrogen atom, a halogen atom, a substituted or unsubstituted alkyl group having 1 to 10 carbon atoms, a substituted or unsubstituted aryl group having 6 to 14 carbon atoms, a substituted or unsubstituted acetal group, or a substituted or unsubstituted hydroxyl group.

The light absorbent of the present invention can be synthesized by conventional methods, but preferably, synthesis of the light absorbent of the present invention is achieved by a reaction in a basic environment.

The aforementioned various dianhydrides are advantageous in that the compounds are highly reactive with alcohols, and have four reactive groups so that two chromophores can be introduced first and then two more crosslinking sites can be provided in the subsequent processes.

Examples of the base that can be used to provide a basic environment include dimethylaminopyridine, pyridine, 1,4-diazabicyclo[2,2,2]octane, 1,5-diazabicyclo[4,3,0]nonane, triethylamine, 2,6-di-tert-butylpyridine, diisopropylethylamine, diazabicycloundecene, tetramethylethylenediamine, tetrabutylammonium bromide and the like, and no particular limitation is posed.

As for the solvent for synthesis, one or more can be selected from benzene, toluene, xylene, halogenated benzene, diethyl ether, tetrahydrofuran, esters, ethers, lactones, ketones and amides, and used.

The temperature for synthesis of the compound can be selected and used in accordance with the solvent, and is usually 5° C. to 200° C., and preferably 20° C. to 100° C.

According to another aspect of the present invention, an organic anti-reflective layer composition containing the light absorbent of the present invention is also provided.

According to an embodiment of the present invention, the organic anti-reflective layer composition comprises the light absorbent of the present invention, a polymer, a thermal acid generating agent, a crosslinking agent and a solvent.

A preferable organic anti-reflective layer composition needs to satisfy the following requirements.

Firstly, the composition should contain a substance which is capable of absorbing light in the wavelength region of the light source for exposure so as to prevent reflection from underneath film layers.

Secondly, in a process of laminating an anti-reflective layer and then laminating a photoresist layer, the anti-reflective layer should not be dissolved and destroyed by the solvent for the photoresist. For this reason, the anti-reflective layer should be designed to have a structure which can be thermally cured, and during the process of laminating the anti-reflective layer, a baking process is carried out after coating of the anti-reflective layer so as to proceed curing.

Thirdly, the anti-reflective layer should be able to be etched more rapidly than the photoresist layer on the upper side, so that the loss of photoresist resulting from etching of underneath film layers can be reduced.

Fourthly, the anti-reflective layer composition should not be reactive to the photoresist on the upper side. Further, compounds such as amines or acids should be prevented from migrating to the photoresist layer. This is because these migrating impurities may cause defects, such as footing or undercut in particular, in the photoresist pattern.

Fifthly, the anti-reflective layer composition should have optical properties which are suitable for various exposure processes using various substrates, that is, appropriate refractive index and absorption coefficient, and should have good adhesive power to the substrate and photoresist layer.

The organic anti-reflective layer composition according to the present invention satisfies all of the above-mentioned requirements.

Hereinafter, the organic anti-reflective layer composition according to the present invention will be described in detail.

The light absorbent is a compound represented by formula 1 or formula 2 as described previously in the above. The polymer to be contained in the organic anti-reflective layer composition of the present invention can be obtained by polymerizing an acrylate-based, maleic anhydride-based, phenol-based or ester-based monomer, and the polymer is not particularly limited as long as it is a polymer having crosslinking sites which are capable of reacting with the light absorbent, at the terminals of the main chain or side chains.

An organic anti-reflective layer employing such polymer acquires resistance to dissolution by solvents, as the composition applied on a substrate is cured while going through a baking process.

Therefore, at the time of applying a photosensitizer after the lamination of the organic anti-reflective layer, dissolution of the anti-reflective layer by the solvent of the photosensitizer does not occur, and stability can be imparted to the anti-reflective layer.

The organic anti-reflective layer composition of the present invention may contain additives in order to facilitate curing of the light absorbent and polymer and to enhance their performance, and examples of such additives include a crosslinking agent and a thermal acid generating agent.

First, the crosslinking agent is preferably a compound having at least two or more crosslinkable functional groups, and examples thereof include aminoplastic compounds, polyfunctional epoxy resins, mixtures of dianhydrides, and the like.

The aminoplastic compounds may be exemplified by dimethoxymethylglycoluril, diethoxymethylglycoluril and mixtures thereof, diethyldimethylmethylglycoluril, tetramethoxymethylglycoluril, hexamethoxymethylmelamine resin, and the like.

As for the polyfunctional epoxy compounds, it is preferable to use, for example, MY720, CY179MA, DENACOL and the like, as well as products equivalent thereto.

Next, it is preferable to use a thermal acid generating agent as a catalyst for accelerating the curing reaction. As for the thermal acid generating agent to be contained in the present invention, toluenesulfonic acid, amine salts or pyridine salts of toluenesulfonic acid, alkylsulfonic acid, amine salts or pyridine salts of alkylsulfonic acid, and the like can also be used.

As for the organic solvent that can be used in the organic anti-reflective layer composition of the present invention, it is preferable to use one or more solvents selected from the group consisting of propylene glycol monomethyl ether (PGME), propylene glycol monomethyl ether acetate (PGMEA), cyclohexanone, ethyl lactate, propylene glycol n-propyl ether, dimethylformamide (DMF), γ-butyrolactone, ethoxyethanol, methoxyethanol, methyl 3-methoxypropionate (MMP) and ethyl 3-ethoxypropionate (EEP).

According to another embodiment of the present invention, the organic anti-reflective layer composition contains the light absorbent represented by formula 1 or formula 2 in an amount of preferably 0.1 to 40% by weight, more preferably 0.1 to 15% by weight, and even more preferably 0.1 to 10% by weight, based on the whole composition. The polymer is contained in an amount of preferably 0.1 to 20% by weight based on the whole composition. The crosslinking agent is contained in an amount of preferably 0.01 to 15% by weight, and more preferably 0.05 to 7% by weight, based on the whole composition. The thermal acid generating agent is contained in an amount of 0.01 to 20% by weight, more preferably 0.01 to 10% by weight, and even more preferably 0.02 to 5% by weight, based on the whole composition. The balance of the contents in the composition can be constituted of the solvent and other additional additives which are well known and widely used.

When the processes for forming an organic anti-reflective layer are briefly examined, an organic anti-reflective layer composition containing the constituent components as described above at the compositional ratios given above is applied on a wafer, and then a thermal process such as baking is carried out so that acid is generated from the thermal acid generating agent. Then, in the presence of the generated acid, a crosslinking reaction involving the light absorbent represented by formula 1 or formula 2, the polymer and the crosslinking agent which is used as an additive, is accelerated, and an organic anti-reflective layer which is not soluble in organic solvents is formed. Such organic anti-reflective layer can prevent diffused reflection from the layers underneath the photoresist layer by absorbing far-ultraviolet rays which have penetrated through the photoresist layer and reached the organic anti-reflective layer.

The method for forming a pattern of a semiconductor device using the organic anti-reflective layer composition as described above, comprises applying the organic anti-reflective layer composition on top of a layer to be etched; curing the applied composition through a baking process, and forming crosslinking bonds to form an organic anti-reflective layer; applying a photoresist on top of the organic anti-reflective layer, and exposing and developing the photoresist to form a photoresist pattern; and etching the organic anti-reflective layer using the photoresist pattern as an etching mask, and then etching the layer to be etched so as to pattern the layer to be etched.

In the process of laminating the organic anti-reflective layer according to the present invention, the baking process can be carried out preferably at a temperature of 150° C. to 250° C. for 0.5 to 5 minutes, and more preferably for 1 minute to 5 minutes.

Furthermore, in the patterning method according to the present invention, an additional baking process can be carried out again before or after laminating an organic or inorganic composition of anti-reflective layer or silicone anti-reflective layer on top of a spin-on carbon hard mask, and such baking process is preferably carried out at a temperature of 70° C. to 200° C.

According to another aspect of the present invention, a semiconductor device produced by the patterning method of the present invention is provided.

The present invention will be described specifically by way of the following Synthesis Examples and Examples. However, the present invention is not intended to be limited to these Synthesis Examples and Examples.

In the following Synthesis Examples 1 to 10, light absorbents for organic anti-reflective layer were synthesized.

Synthesis Example 1

50 g of bicycle[2,2,2]octene-2,3,5,6-tetracarboxylic acid dianhydride, 43.57 g of benzenemethanol, 31.87 g of pyridine and 4.92 g of dimethylaminopyridine were dissolved in 260.73 g of 1,4-dioxane, and then the solution was allowed to react at 80° C. for 24 hours. After completion of the reaction, formic acid was added dropwise to the reaction solution to neutralize the solution. Ethyl acetate and distilled water were added to this reaction product, and the organic layer was separated. The separated organic layer was subjected to solvent removal, and then was dissolved again in dioxane. This solution was dropped in water, and a precipitate thus generated was filtered, washed several times with distilled water, and then dried, to obtain 45.62 g (yield=46.6%) of a compound. The $^1$H-NMR spectrum of the copolymer produced according to Synthesis Example 1 is presented in FIG. 1.

Synthesis Example 2

Figure 2:
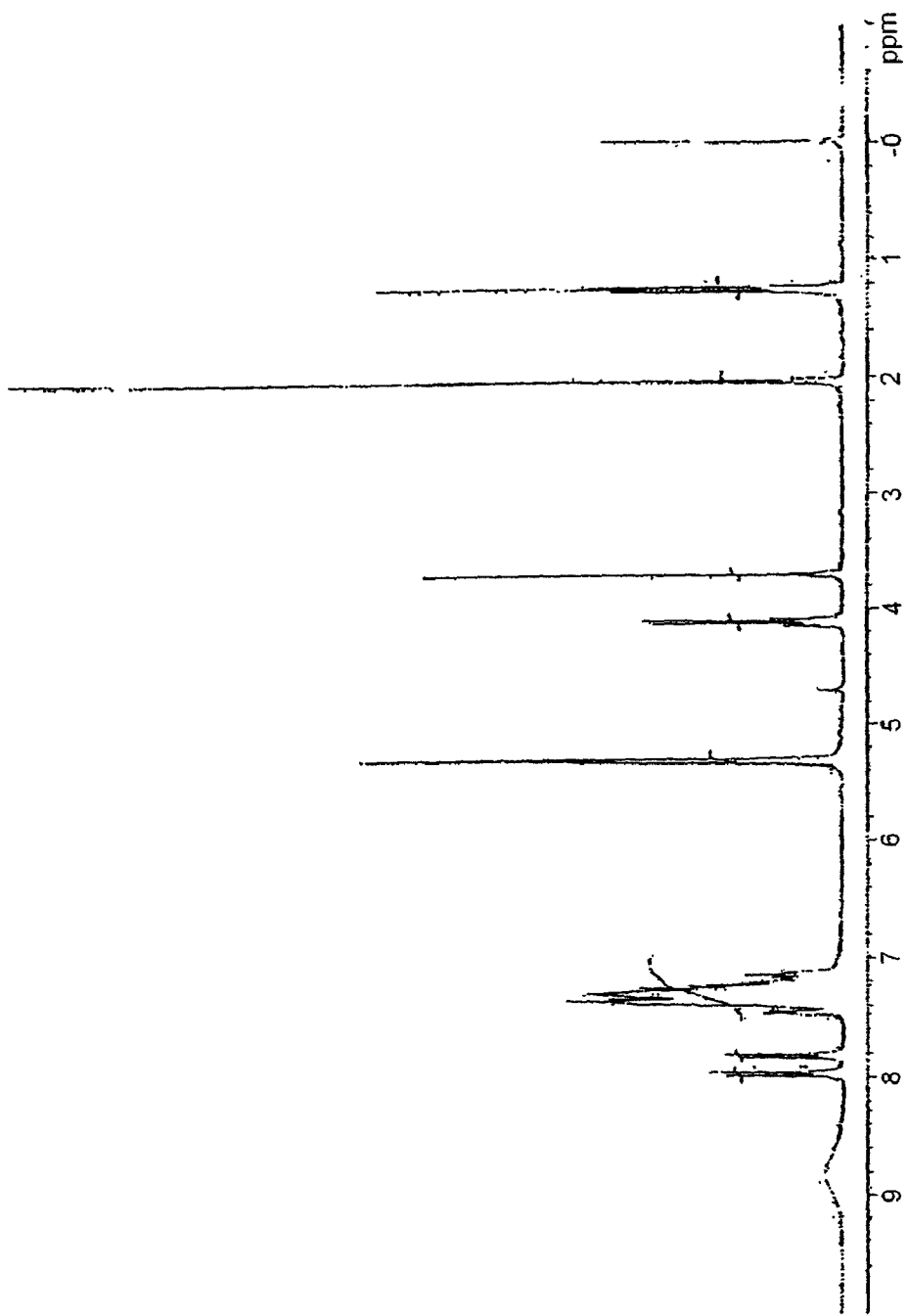
FIG. 2 is a $^1$H-NMR spectrum of a copolymer produced according to another embodiment of the present invention.

105 g of 4,4'-oxydiphthalic anhydride, 73.21 g of benzenemethanol, 5.36 g of pyridine, and 8.27 g of dimethylaminopyridine were dissolved in 450.21 g of 1,4-dioxane, and then the solution was allowed to react at 80° C. for 24 hours. After completion of the reaction, formic acid was added dropwise to the reaction solution to neutralize the solution. Ethyl acetate and distilled water were added to this reaction product, and the organic layer was separated. The separated organic layer was subjected to solvent removal, and then was dissolved in propylene glycol monomethyl ether acetate, to obtain a compound. The $^1$H-NMR spectrum of the solid light absorbent produced according to Synthesis Example 2 is presented in FIG. 2.

Synthesis Example 3

Figure 3:
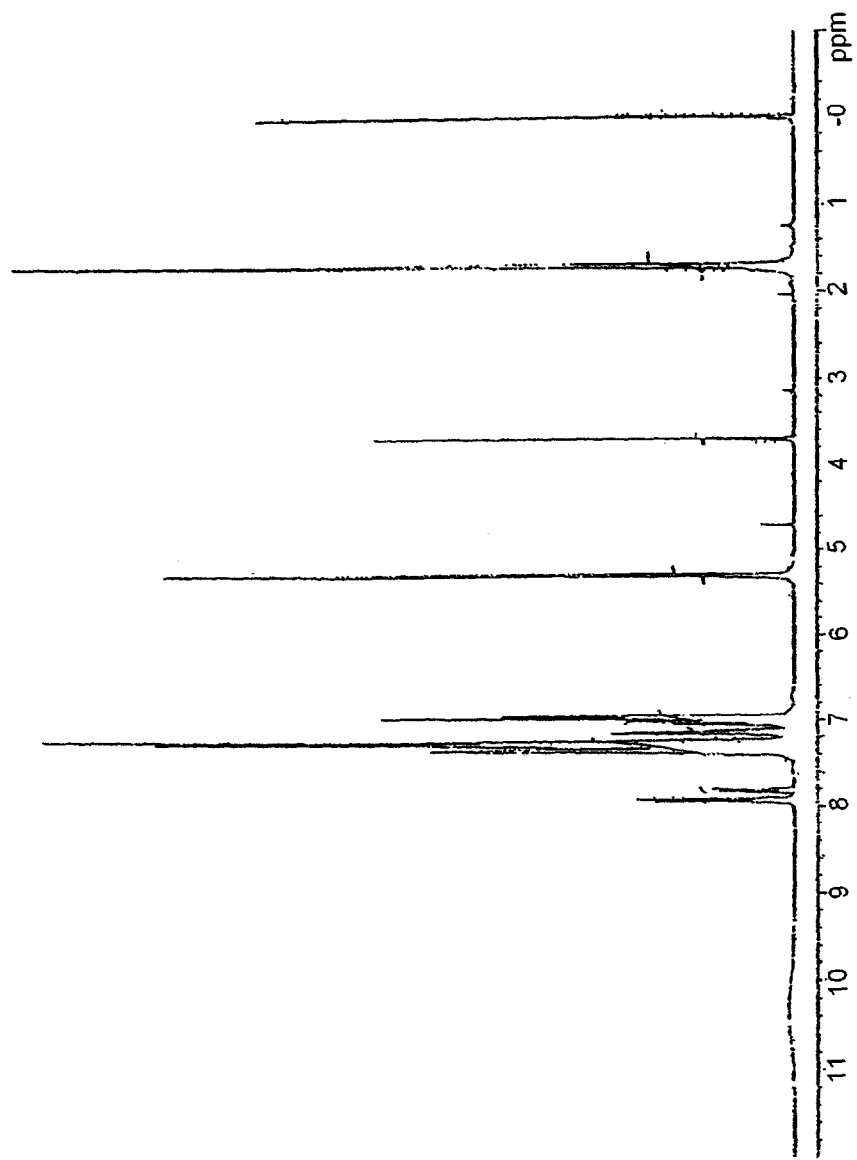
FIG. 3 is a $^1$H-NMR spectrum of a copolymer produced according to another embodiment of the present invention.

50 g of 4,4'-(4,4'-isopropylidenediphenoxy)bis(phthalic anhydride), 19.74 g of benzyl alcohol, 15.2 g of pyridine, and 2.35 g of dimethylaminopyridine were dissolved in 174.56 g of 1,4-dioxane, and then the solution was allowed to react at 80° C. for 24 hours. After completion of the reaction, formic acid was added dropwise to the reaction solution to neutralize the solution. Ethyl acetate and distilled water were added to this reaction product, and the organic layer was separated. The separated organic layer was subjected to solvent removal, and then was dissolved in propylene glycol monomethyl ether acetate, to obtain a compound. The $^1$H-NMR spectrum of the solid light absorbent produced according to Synthesis Example 3 is presented in FIG. 3.

Synthesis Example 4

Figure 4:
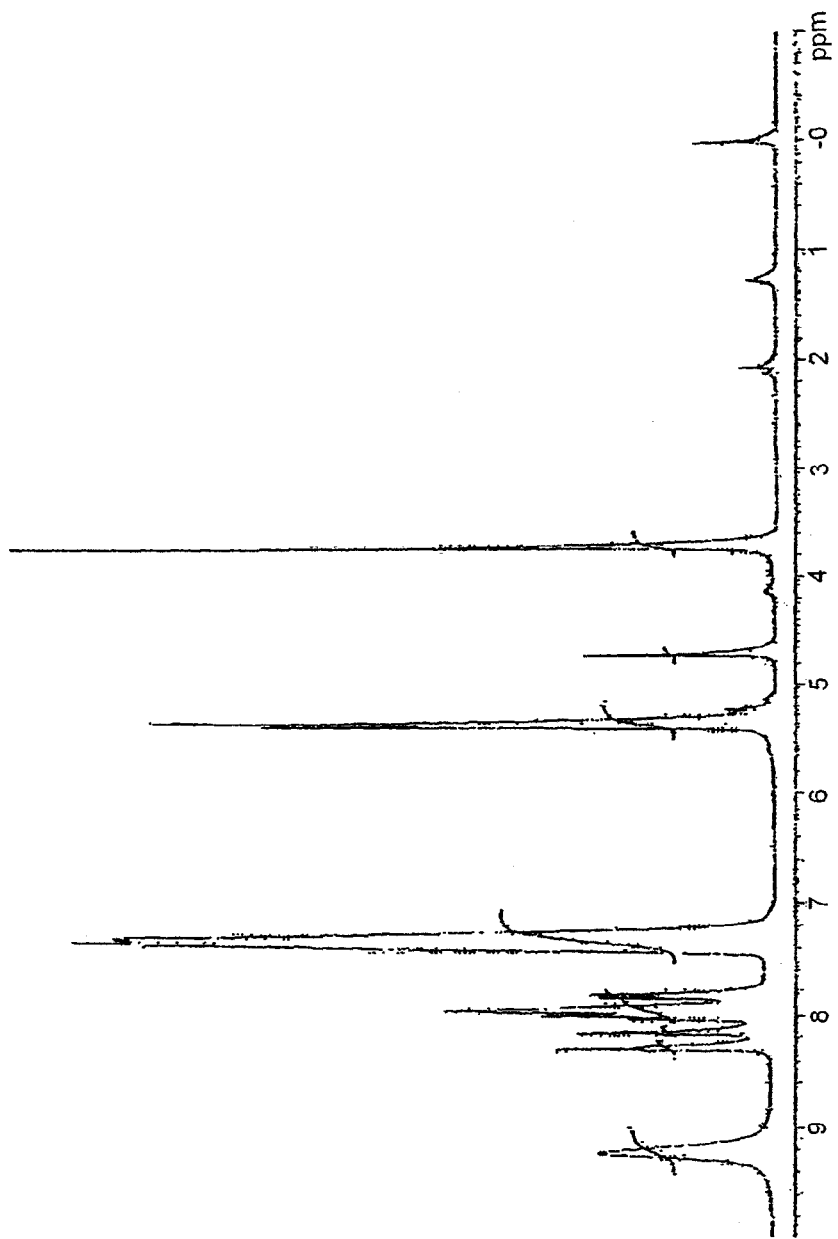
FIG. 4 is a $^1$H-NMR spectrum of a copolymer produced according to another embodiment of the present invention.

50 g of benzophenone-3,3',4,4'-tetracarboxylic acid dianhydride, 33.56 g of benzyl alcohol, 24.55 g of pyridine, and 3.79 g of dimethylaminopyridine were dissolved in 223.8 g of 1,4-dioxane, and then the solution was allowed to react at 80° C. for 24 hours. After completion of the reaction, formic acid was added dropwise to the reaction solution to neutralize the solution. Ethyl acetate and distilled water were added to this reaction product, and the organic layer was separated. The separated organic layer was subjected to solvent removal, and then was dissolved in propylene glycol monomethyl ether acetate, to obtain a compound. The $^1$H-NMR spectrum of the solid light absorbent produced according to Synthesis Example 4 is presented in FIG. 4.

Synthesis Example 5

Figure 5:
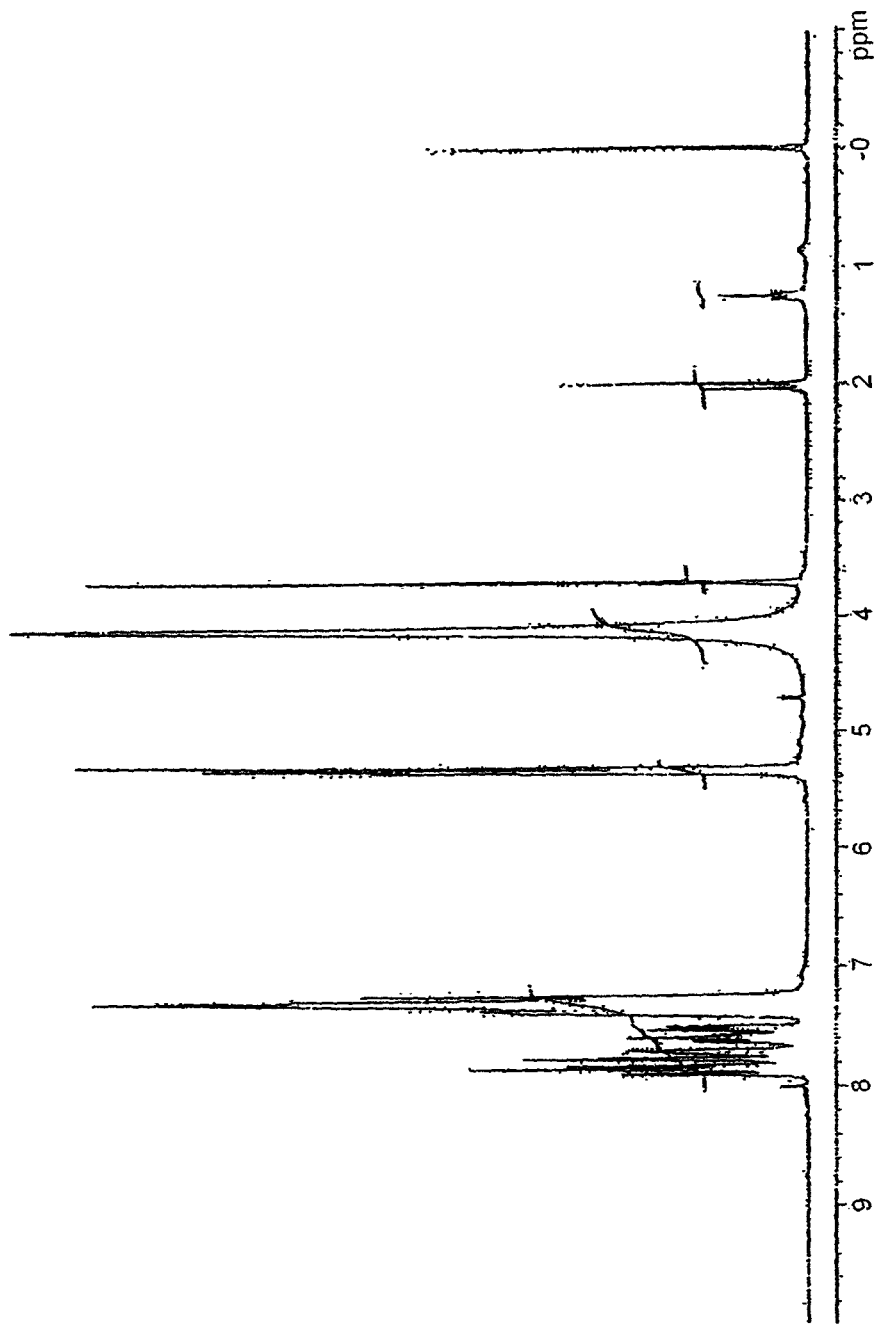
FIG. 5 is a $^1$H-NMR spectrum of a copolymer produced according to another embodiment of the present invention.

25 g of 4,4'-(hexafluoroisopropylidene)diphthalic anhydride, 12.17 g of benzyl alcohol, 8.9 g of pyridine, and 1.38 g of dimethylaminopyridine were dissolved in 94.9 g of 1,4-dioxane, and then the solution was allowed to react at 80° C. for 24 hours. After completion of the reaction, formic acid was added dropwise to the reaction solution to neutralize the solution. Ethyl acetate and distilled water were added to this reaction product, and the organic layer was separated. The separated organic layer was subjected to solvent removal, and then was dissolved in propylene glycol monomethyl ether acetate, to obtain a compound. The $^1$H-NMR spectrum of the solid light absorbent produced according to Synthesis Example 5 is presented in FIG. 5.

Synthesis Example 6

Figure 6:
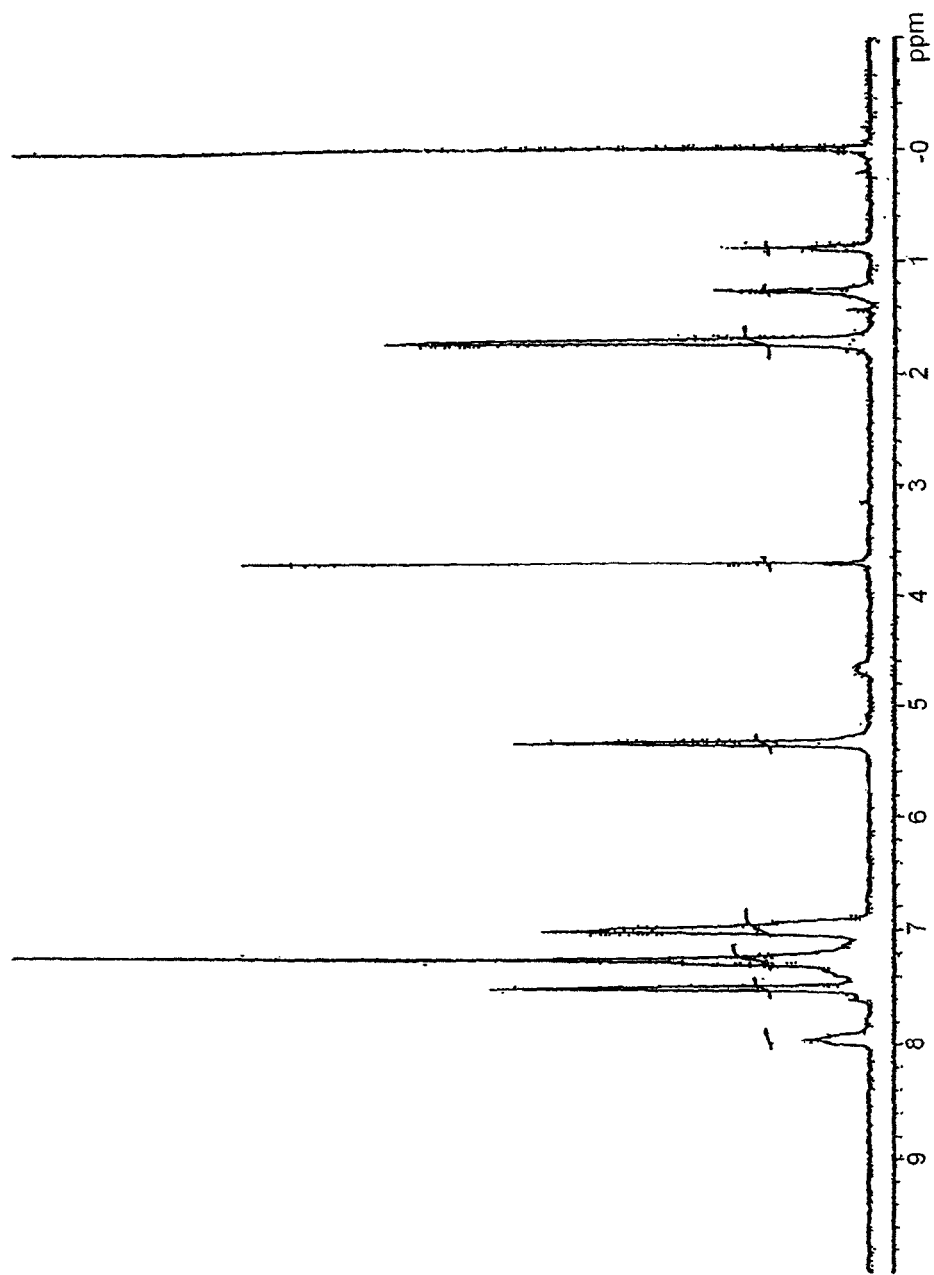
FIG. 6 is a $^1$H-NMR spectrum of a copolymer produced according to another embodiment of the present invention.

20 g of 4,4'-(4,4'-isopropylidenediphenoxy)bis(phthalic anhydride), 5.31 g of benzenedimethanol, 3.04 g of pyridine, and 0.74 g of dimethylaminopyridine were dissolved in 57.64 g of 1,4-dioxane, and then the solution was allowed to react at 80° C. for 24 hours. After completion of the reaction, formic acid was added dropwise to the reaction solution to neutralize the solution. Ethyl acetate and distilled water were added to this reaction product, and the organic layer was separated. The separated organic layer was subjected to solvent removal, and then was dissolved in propylene glycol monomethyl ether acetate, to obtain a compound. The $^1$H-NMR spectrum of the solid light absorbent produced according to Synthesis Example 6 is presented in FIG. 6.

Synthesis Example 7

Figure 7:
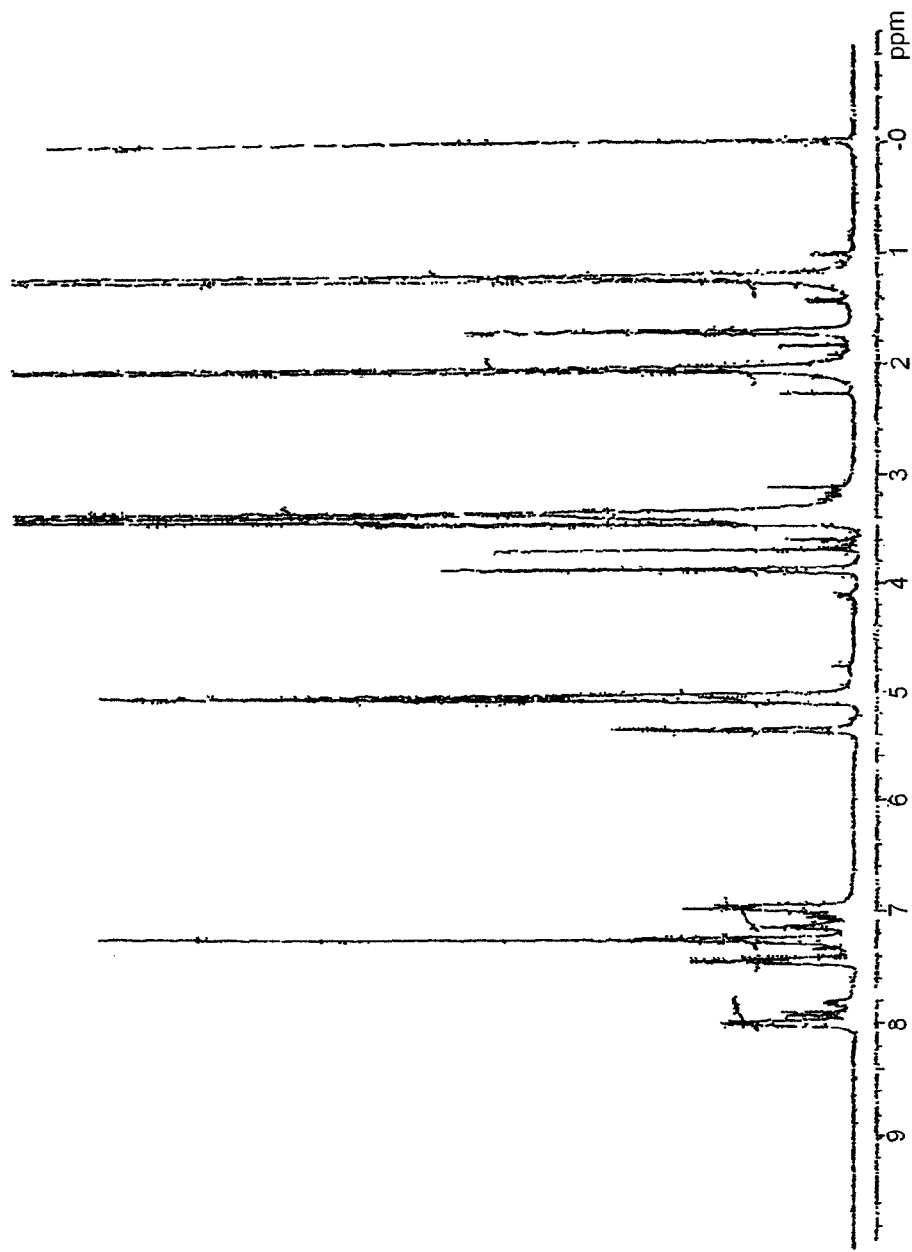
FIG. 7 is a $^1$H-NMR spectrum of a copolymer produced according to another embodiment of the present invention.

50 g of 4,4'-(4,4'-isopropylidenediphenoxy)bis(phthalic anhydride), 27.28 g of 4-(hydroxymethyl)benzoic acid, 15.2 g of pyridine, and 2.35 g of dimethylaminopyridine were dissolved in 174.56 g of 1,4-dioxane, and then the solution was allowed to react at 80° C. for 24 hours. After completion of the reaction, formic acid was added dropwise to the reaction solution to neutralize the solution. Ethyl acetate and distilled water were added to this reaction product, and the organic layer was separated. The separated organic layer was subjected to solvent removal, and then was dissolved in propylene glycol monomethyl ether acetate, to obtain a compound. The $^1$H-NMR spectrum of the solid light absorbent produced according to Synthesis Example 7 is presented in FIG. 7.

Synthesis Example 8

Figure 8:
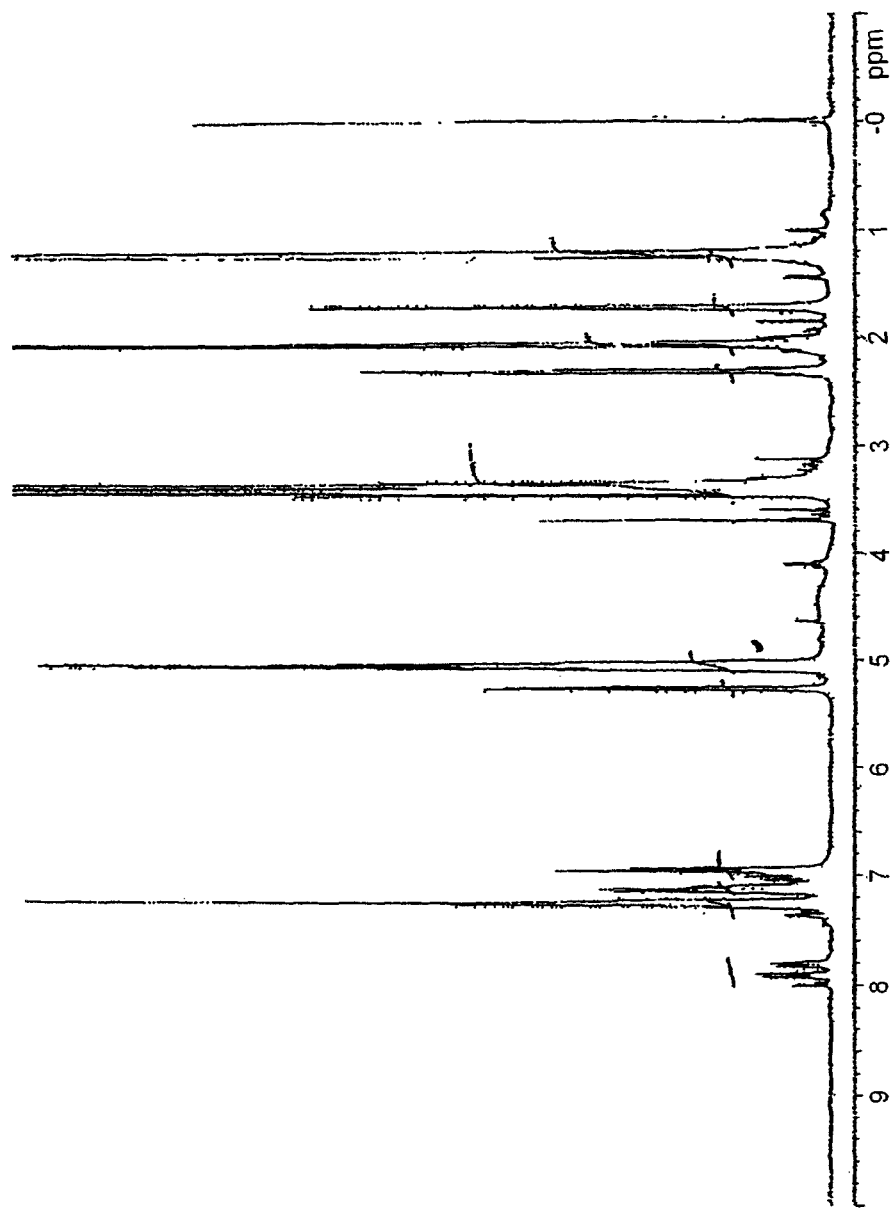
FIG. 8 is a $^1$H-NMR spectrum of a copolymer produced according to another embodiment of the present invention.

50 g of 4,4'-(4,4'-isopropylidenediphenoxy)bis(phthalic anhydride), 31.39 g of methyl 4-(hydroxymethyl)benzoate, 15.2 g of pyridine, and 2.35 g of dimethylaminopyridine were dissolved in 174.56 g of 1,4-dioxane, and then the solution was allowed to react at 80° C. for 24 hours. After completion of the reaction, formic acid was added dropwise to the reaction solution to neutralize the solution. Ethyl acetate and distilled water were added to this reaction product, and the organic layer was separated. The separated organic layer was subjected to solvent removal, and then was dissolved in propylene glycol monomethyl ether acetate, to obtain a compound. The $^1$H-NMR spectrum of the solid light absorbent produced according to Synthesis Example 8 is presented in FIG. 8.

Synthesis Example 9

Figure 9:
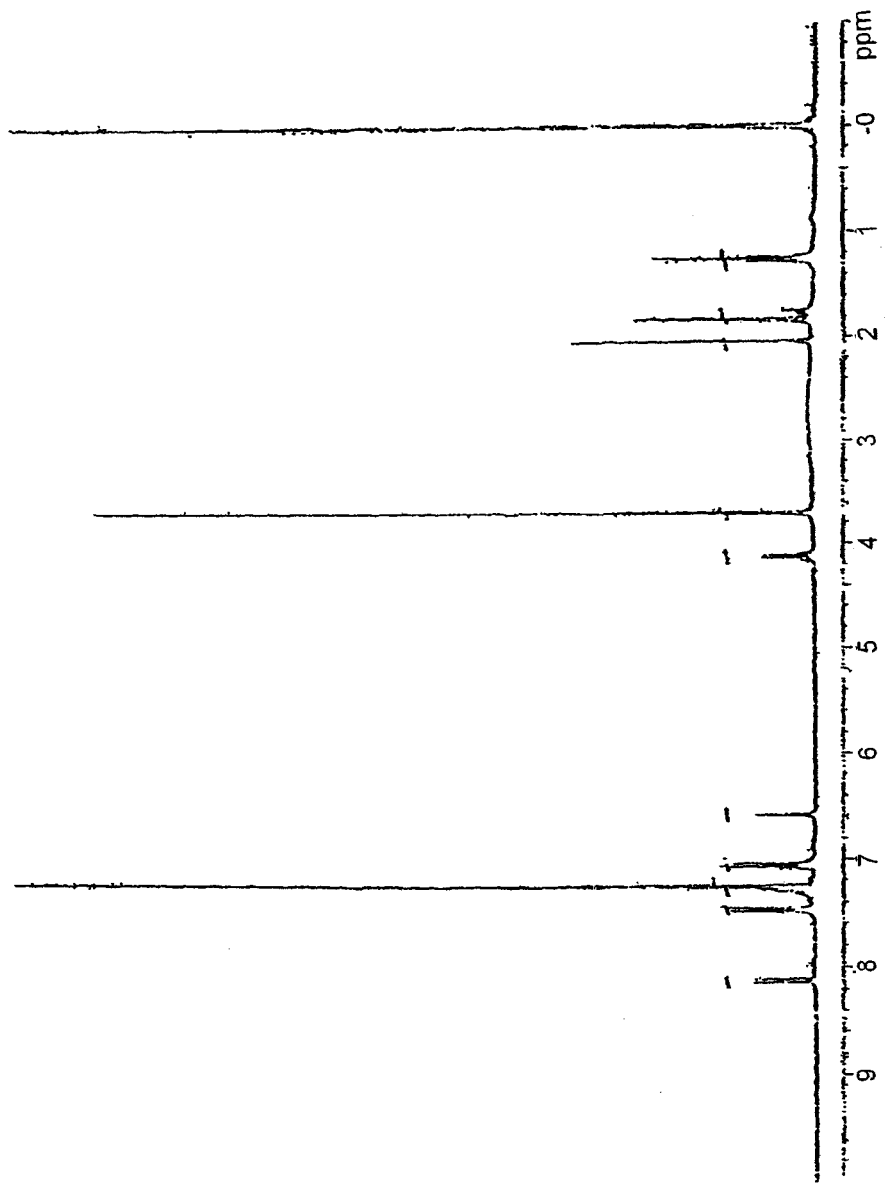
FIG. 9 is a $^1$H-NMR spectrum of a copolymer produced according to another embodiment of the present invention.

50 g of 4,4'-(4,4'-isopropylidenediphenoxy)bis(phthalic anhydride), 23.47 g of 4-methylbenzyl alcohol, 15.2 g of pyridine, and 2.35 g of dimethylaminopyridine were dissolved in 174.56 g of 1,4-dioxane, and then the solution was allowed to react at 80° C. for 24 hours. After completion of the reaction, formic acid was added dropwise to the reaction solution to neutralize the solution. Ethyl acetate and distilled water were added to this reaction product, and the organic layer was separated. The separated organic layer was subjected to solvent removal, and then was dissolved in propylene glycol monomethyl ether acetate, to obtain a compound. The $^1$H-NMR spectrum of the solid light absorbent produced according to Synthesis Example 9 is presented in FIG. 9.

Synthesis Example 10

50 g of 4,4'-(4,4'-isopropylidenediphenoxy)bis(phthalic anhydride), 23.85 g of 4-hydroxybenzyl alcohol, 15.2 g of pyridine, and 2.35 g of dimethylaminopyridine were dissolved in 174.56 g of 1,4-dioxane, and then the solution was allowed to react at 80° C. for 24 hours. After completion of the reaction, formic acid was added dropwise to the reaction solution to neutralize the solution. Ethyl acetate and distilled water were added to this reaction product, and the organic layer was separated. The separated organic layer was subjected to solvent removal, and then was dissolved in propylene glycol monomethyl ether acetate, to obtain a compound. The $^1$H-NMR spectrum of the solid light absorbent produced according to Synthesis Example 10 is presented in FIG. 10.

Example 1

Preparation of Organic Anti-Reflective Layer Composition A 4 g of the light absorbent for organic anti-reflective layer produced in the above Synthesis Example 1, 6 g of an acrylic polymer, 2 g of tetramethoxymethylglycoluril and 0.2 g of pyridinium p-toluenesulfonate were dissolved in 987.8 g of propylene glycol monomethyl ether acetate, and then the solution was filtered through a membrane filter having a pore size of 0.2 µm, to prepare an organic anti-reflective layer composition A.

Example 2

Preparation of Organic Anti-Reflective Layer Composition B 4 g of the light absorbent for organic anti-reflective layer produced in the above Synthesis Example 2, 6 g of an acrylic polymer, 2 g of tetramethoxymethylglycoluril and 0.2 g of pyridinium p-toluenesulfonate were dissolved in 987.8 g of propylene glycol monomethyl ether acetate, and then the solution was filtered through a membrane filter having a pore size of 0.2 µm, to prepare an organic anti-reflective layer composition B.

Example 3

Preparation of Organic Anti-Reflective Layer Composition C 4 g of the light absorbent for organic anti-reflective layer produced in the above Synthesis Example 3, 6 g of an acrylic polymer, 2 g of tetramethoxymethylglycoluril and 0.2 g of pyridinium p-toluenesulfonate were dissolved in 987.8 g of propylene glycol monomethyl ether acetate, and then the solution was filtered through a membrane filter having a pore size of 0.2 µm, to prepare an organic anti-reflective layer composition C.

Example 4

Preparation of Organic Anti-Reflective Layer Composition D 4 g of the light absorbent for organic anti-reflective layer produced in the above Synthesis Example 4, 6 g of an acrylic polymer, 2 g of tetramethoxymethylglycoluril and 0.2 g of pyridinium p-toluenesulfonate were dissolved in 987.8 g of propylene glycol monomethyl ether acetate, and then the solution was filtered through a membrane filter having a pore size of 0.2 µm, to prepare an organic anti-reflective layer composition D.

Example 5

Preparation of Organic Anti-Reflective Layer Composition E 4 g of the light absorbent for organic anti-reflective layer produced in the above Synthesis Example 5, 6 g of an acrylic polymer, 2 g of tetramethoxymethylglycoluril and 0.2 g of pyridinium p-toluenesulfonate were dissolved in 987.8 g of propylene glycol monomethyl ether acetate, and then the solution was filtered through a membrane filter having a pore size of 0.2 µm, to prepare an organic anti-reflective layer composition E.

Example 6

Preparation of Organic Anti-Reflective Layer Composition F 4 g of the light absorbent for organic anti-reflective layer produced in the above Synthesis Example 6, 6 g of an acrylic polymer, 2 g of tetramethoxymethylglycoluril and 0.2 g of pyridinium p-toluenesulfonate were dissolved in 987.8 g of propylene glycol monomethyl ether acetate, and then the solution was filtered through a membrane filter having a pore size of 0.2 µm, to prepare an organic anti-reflective layer composition F.

Example 7

Preparation of Organic Anti-Reflective Layer Composition G 4 g of the light absorbent for organic anti-reflective layer produced in the above Synthesis Example 7, 6 g of an acrylic polymer, 2 g of tetramethoxymethylglycoluril and 0.2 g of pyridinium p-toluenesulfonate were dissolved in 987.8 g of propylene glycol monomethyl ether acetate, and then the solution was filtered through a membrane filter having a pore size of 0.2 µm, to prepare an organic anti-reflective layer composition G.

Example 8

Preparation of Organic Anti-Reflective Layer Composition H 4 g of the light absorbent for organic anti-reflective layer produced in the above Synthesis Example 8, 6 g of an acrylic polymer, 2 g of tetramethoxymethylglycoluril and 0.2 g of pyridinium p-toluenesulfonate were dissolved in 987.8 g of propylene glycol monomethyl ether acetate, and then the solution was filtered through a membrane filter having a pore size of 0.2 µm, to prepare an organic anti-reflective layer composition H.

Example 9

Preparation of Organic Anti-Reflective Layer Composition I 4 g of the light absorbent for organic anti-reflective layer produced in the above Synthesis Example 9, 6 g of an acrylic polymer, 2 g of tetramethoxymethylglycoluril and 0.2 g of pyridinium p-toluenesulfonate were dissolved in 987.8 g of propylene glycol monomethyl ether acetate, and then the solution was filtered through a membrane filter having a pore size of 0.2 µm, to prepare an organic anti-reflective layer composition I.

Example 10

Preparation of Organic Anti-Reflective Layer Composition J 4 g of the light absorbent for organic anti-reflective layer produced in the above Synthesis Example 10, 6 g of an acrylic polymer, 2 g of tetramethoxymethylglycoluril and 0.2 g of pyridinium p-toluenesulfonate were dissolved in 987.8 g of propylene glycol monomethyl ether acetate, and then the solution was filtered through a membrane filter having a pore size of 0.2 µm, to prepare an organic anti-reflective layer composition J.

Results for Measurement of Properties of Organic Anti-Reflective Layers and Formation of Photoresist Patterns 1) Stripping Test Each of the organic anti-reflective layer compositions A to J prepared in Example 1 to 10 was applied on a silicon wafer by spin coating, and then the coated wafer was baked on a hot plate at 230° C. for 1 minute to form an organic anti-reflective layer. The thickness of the layer was measured, and the wafer coated with the organic anti-reflective layer was immersed for 1 minute in ethyl lactate and propylene glycol monomethyl ether, which are solvents used for the photoresist. Subsequently, the coated wafer was baked on a hot plate at 100° C. for 1 minute to completely remove the solvents, and then the thickness of the organic anti-reflective layer was measured again. It was confirmed that the anti-reflective layer was insoluble in the solvents.

2) Measurement of Optical Properties

Each of the organic anti-reflective layer compositions A to J prepared in Example 1 to 10 was applied on a silicon wafer by spin coating, and then the coated wafer was baked on a hot plate at 230° C. for 1 minute to form an organic anti-reflective layer. The refractive index (n) at 193 nm and the extinction coefficient (k) of the anti-reflective layer were measured using a spectroscopic ellipsometer (J.A. Woollam Co., Inc.). The measurement results are presented in Table 1.

TABLE 1

|  | Refractive index (n) | Extinction coefficient (k) | Thickness of first microthin film (nm) | Reflectance (%) |
| --- | --- | --- | --- | --- |
| Example 1 | 1.62 | 0.28 | 33 | <0.1 |
| Example 2 | 1.76 | 0.28 | 24 | <0.1 |
| Example 3 | 1.75 | 0.29 | 24 | <0.1 |
| Example 4 | 1.79 | 0.33 | 22 | <0.1 |
| Example 5 | 1.69 | 0.37 | 27 | <0.2 |
| Example 6 | 1.67 | 0.28 | 30 | <0.1 |
| Example 7 | 1.65 | 0.29 | 31 | <0.1 |
| Example 8 | 1.68 | 0.29 | 29 | <0.1 |
| Example 9 | 1.67 | 0.25 | 30 | <0.1 |
| Example 10 | 1.66 | 0.25 | 31 | <0.1 |

3) Simulation of First Microthin Film

An organic anti-reflective layer was formed using each of the organic anti-reflective layer compositions A to J prepared in Example 1 to 10, and then the refractive index (n) at 193 nm and the extinction coefficient (k) of the anti-reflective layer were measured using a spectroscopic ellipsometer. Subsequently, the thickness of the first microthin film, and the reflectance in the case of using the thickness of the first microthin film were calculated by performing a simulation using the values of the refractive index (n) and extinction coefficient (k) obtained from the measurement. The simulation was related to the reflectance obtainable in the case where 40 nm of silicon oxynitride was deposited on the silicon wafer. The software used in the simulation was KLA Tencor FINDLE Division PROLITH, and the results are presented in Table 1.

4) Formation of Organic Anti-Reflective Layer and Photoresist Pattern

Each of the organic anti-reflective layer compositions A to J prepared in Example 1 to 10 was applied by spin coating on a silicon wafer deposited with silicon oxynitride, and then the coated wafer was baked on a hot plate at 230° C. for 1 minute, to form an organic anti-reflective layer. Subsequently, an ArF photoresist was applied on top of the organic anti-reflective layer, and then the coated wafer was baked at 100° C. for 60 seconds. Then, the photoresist was exposed using a scanner equipment, and then the wafer was baked again at 115° C. for 60 seconds. The exposed wafer was developed using a developer solution containing 2.380 by weight of TMAH, to obtain a final photoresist pattern. The pattern was of L/S type with a size of 80 nm, and the results are presented in Table 2.

TABLE 2

|  | Energy margin (%) | Focus depth margin (μm) | Shape of pattern |
| --- | --- | --- | --- |
| Example 1 | 22 | 0.4 | Perpendicular |
| Example 2 | 20 | 0.5 | Perpendicular |
| Example 3 | 23 | 0.5 | Perpendicular |
| Example 4 | 26 | 0.3 | Perpendicular |
| Example 5 | 31 | 0.5 | Perpendicular |
| Example 6 | 28 | 0.4 | Perpendicular |
| Example 7 | 27 | 0.4 | Perpendicular |
| Example 8 | 26 | 0.5 | Perpendicular |
| Example 9 | 28 | 0.4 | Perpendicular |
| Example 10 | 31 | 0.3 | Perpendicular |

What is claimed is:

1. An organic anti-reflective layer composition comprising a light absorbent represented by the following formula 1, a polymer, a thermal acid generating agent, a crosslinking agent and a solvent:

[Formula 1]

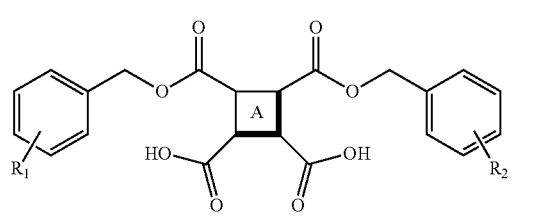

wherein A represents a substituted or unsubstituted, linear or branched, saturated tetravalent hydrocarbon group having 1 to 20 carbon atoms, a substituted or unsubstituted, linear or branched, saturated hydrocarbon group having 1 to 20 carbon atoms and containing one or more heteroatoms, a substituted or unsubstituted aromatic group having 4 to 20 carbon atoms, a substituted or unsubstituted heteroaromatic group having 3 to 20 carbon atoms, a substituted or unsubstituted alicyclic group having 4 to 20 carbon atoms, a substituted or unsubstituted heteroalicyclic group having 3 to 20 carbon atoms, a substituted or unsubstituted diaryl ether having 3 to 20 carbon atoms, a substituted or unsubstituted diaryl sulfide having 3 to 20 carbon atoms, a substituted or unsubstituted diaryl sulfoxide having 3 to 20 carbon atoms, a substituted or unsubstituted diaryl ketone having 3 to 20 carbon atoms, or a substituted or unsubstituted diaryl bisphenol A having 3 to 20 carbon atoms; $R_1$ and $R_2$ each independently represent a hydrogen atom, a halogen atom, a substituted or unsubstituted alkyl group having 1 to 10 carbon atoms, a substituted or unsubstituted aryl group having 6 to 14 carbon atoms, a substituted or unsubstituted acetal group, or a hydroxyl group; wherein the composition comprises 0.1 to 5% by weight of the light absorbent, 0.1 to 5% by weight of the polymer, 0.01 to 1% by weight of the thermal acid generating agent, and 0.05 to 5% by weight of the crosslinking agent.

2. The organic anti-reflective layer composition according to claim 1, wherein the polymer is a resin having crosslinking sites at the terminals of the main chain or side chains.

3. The organic anti-reflective layer composition according to claim 1, wherein the crosslinking agent is an aminoplastic compound, a polyfunctional epoxy resin, an anhydride or a mixture thereof, which respectively has two or more crosslinkable functional groups.

4. The organic anti-reflective layer composition according to claim 1, wherein the thermal acid generating agent is an amine salt of toluenesulfonic acid, a pyridine salt of toluenesulfonic acid, an amine salt of alkylsulfonic acid, or a pyridine salt of alkylsulfonic acid.

5. The organic anti-reflective layer composition according to claim 1, wherein the solvent is one or more selected from the group consisting of propylene glycol monomethyl ether (PGME), propylene glycol monomethyl ether acetate (PGMEA), cyclohexanone, ethyl lactate, propylene glycol n-propyl ether, dimethylformamide (DMF), γ-butyrolactone, ethoxyethanol, methoxyethanol, methyl 3-methoxypropionate (MMP) and ethyl 3-ethoxypropionate (EEP).

* * * * *